US005958882A

United States Patent [19]
Jameson et al.

[11] Patent Number: 5,958,882
[45] Date of Patent: *Sep. 28, 1999

[54] COMPOUNDS THAT INHIBIT T CELL PROLIFERATION AND METHODS USING THE SAME

[75] Inventors: Bradford A. Jameson; James M. McDonnell, both of Philadelphia, Pa.; Robert Korngold, Cherry Hill, N.J.

[73] Assignee: Thomas Jefferson University, Philadelphia, Pa.

[*] Notice: This patent is subject to a terminal disclaimer.

[21] Appl. No.: 08/730,486

[22] Filed: Oct. 11, 1996

Related U.S. Application Data

[63] Continuation of application No. 08/076,092, Jun. 11, 1993, Pat. No. 5,589,458, which is a continuation-in-part of application No. 07/977,692, Nov. 13, 1992, abandoned.

[51] Int. Cl.$^6$ .......................... A61K 38/00; A61K 38/04; C07K 5/00; C07K 7/00
[52] U.S. Cl. ................................ 514/13; 514/14; 514/15; 514/16; 514/17; 514/18; 530/326; 530/327; 530/328; 530/329; 530/330; 530/331
[58] Field of Search .................................. 514/12, 13, 14, 514/15, 16, 17, 18; 530/330, 331, 324, 326, 327, 329, 328

[56] References Cited

U.S. PATENT DOCUMENTS 5,589,458  12/1996  Jameson et al. ........................... 514/13

FOREIGN PATENT DOCUMENTS

| 0 344 006 | 11/1989 | European Pat. Off. . |
| 0344006 | 11/1989 | European Pat. Off. .......... C07K 7/10 |
| WO 89/03420 | 4/1989 | WIPO . |
| WO 89/09782 | 10/1989 | WIPO . |
| WO 91/17179 | 11/1991 | WIPO . |
| WO 92/02543 | 2/1992 | WIPO . |
| WO 92/09625 | 6/1992 | WIPO . |
| WO 92/09628 | 6/1992 | WIPO . |
| WO 93/12810 | 7/1993 | WIPO . |
| WO 94/04557 | 3/1994 | WIPO . |

OTHER PUBLICATIONS

Bank et al., "Perturbation of the T4 Molecule Transmits a Negative Signal to T Cells", *J. Exp. Med.*, 1985, 162, 1294–1303.
Barber et al., "The CD4 and CD8 Antigens are Coupled to a Protein–Tyrosine Kinase (p56$^{lck}$) that Phosphorylates the CD3 Complex".
Biddison et al., "Possible Involvement of the OKT4 Molecule in T Cell Recognition of Class II HLA Antigens", *J. Exp. Med.*, 1982, 156, 1065–1071.
Carr et al., *J. Biol. Chem.*, 1989, 264(35), 21286–21295.
Dianzani et al., "Molecular Associations on the T Cell Surface Correlate with Immunological Memory", *Eur. J. Immunol.*, 1990, 20, 2249–2257.

Fleury et al., "Mutational Analysis of the Interaction Between CD4 and Class II MHC: Class II Antigens Contact CD4 on a Surface Opposite the gp120–Binding Site", *Cell*, 1991, 66, 1037–1049.
Gay et al., "Functional Interaction Between Human T–cell Protein CD4 and the Major Histocompatibility Complex HLA–DR Antigen", *Nature*, 1987, 328, 626–629.
Glaichenhaus et al., "Requirement for Association of p56$^{lck}$ with CD4 in Antigen–Specific Signal Transduction in T Cells", *Cell*, 1991, 64, 511–520.
Harris et al., *Euro. J. Bioch.*, 1990, 194, 611–620.
Hussey et al., "A Soluble CD4 Protein Selectively Inhibits HIV Replication and Syncytium Formation", *Nature*, 1988, 331, 78–81.
Jameson et al., "Location and Chemical Synthesis of a Binding Site for HIV–1 on the CD4 Protein", *Science*, 1988, 240, 1335–1339.
Jameson, B.A., "Modelling in Peptide Design", *Nature*, 1989, 341, 465.
Janeway, C.A., "The Co–Receptor Function of CD4", *Sem. Immunol.*, 1991, 3, 153–160.
Janeway et al., "Cross–Linking and Conformational Change in T–Cell Receptors: Role In Activation and In Repertoire Selection", *CSH Symp. Quant. Biol.*, 1989, LIV, 657–666.
Korngold et al., "Variable Capacity of L3T4$^+$ T Cells to Cause Lethal Graft–Versus–Host Disease Across Minor Histocompatibility Barriers in Mice", *J. Exp. Med.*, 1987, 165, 1552–1564.
Korngold et al., "Acute Experimental Allergic Encephalomyelitis in Radiation Bone Marrow Chimeras Between High and Low Susceptible Strains of Mice", *Immunogens*, 1986, 24, 309–315.
Kumar et al., "A Two–Dimensional Nuclear Overhauser Enhancement (2D NOE) Experiment for the Elucidation of Complete Proton Cross–Relaxation Networks in Biological Macromolecules", *Biochem. Biophys. Res. Commun.*, 1980, 95, 1.
Ledbetter et al., "Signal Transduction Through CD4 Receptors: Stimulatory vs. Inhibitory Activity is Regulated by CD4 Proximity to the CD3/T Cell Receptor", *Eur. J. Immunol.*, 1988, 18, 525–532.
Maddon et al., "The Isolation and Nucleotide Sequence of a cDNA Encoding the T Cell Surface Protein T4: A New Member of the Immunoglobulin Gene Family", *Cell*, 1985, 42, 93–104.

(List continued on next page.)

*Primary Examiner*—Avis M. Davenport
*Attorney, Agent, or Firm*—Woodcock Washburn Kurtz Mackiewicz & Norris, LLP

[57] ABSTRACT

Compounds which display a surface similar to the surface presented by one of five distinct lateral domains of CD4 are disclosed. Methods of treating individuals suspected of suffering from or susceptible to conditions characterized by an undesired immune response comprising administering to the individual at least one compound which mimics a portion of the lateral surface of the CD4 glycoprotein are disclosed.

31 Claims, 15 Drawing Sheets

OTHER PUBLICATIONS

Maddon et al., "The T4 Gene Encodes the AIDS Virus Receptor and is Expressed in the Immune System and the Brain", *Cell,* 1986, 47, 333–348.

Matsui et al., "Low Affinity Interaction of Peptide–MHC Complexes with T Cell Receptors", *Science,* 1991, 254, 1788–1791.

Matthews et al., "Studies on the Leukocyte–Common Antigen: Structure, Function, and Evolutionary Conservation", *CSH Symp. Quant. Biol.,* 1989, LIV, 675–682.

McDonnell et al., "Direct Involvement of the CDR3–Like Domain of CD4 in Helper Cell Activation", *J. Immunol.,* 1992, 149, 1626.

Merrifield, R.B., "Solid Phase Peptide Synthesis. I. The Synthesis of a Tetrapeptide", *J. Am. Chem. Soc.,* 1963, 85, 2149–2154.

Mittler et al., "T–Cell Receptor–CD4 Physical Association in a Murine T–Cell Hybridoma: Induction by Antigen Receptor Ligation", *PNAS USA,* 1989, 86, 8531–8535.

Mittler et al., "Physical Associations Between CD45 and CD4 or CD8 Occur as Late Activation Events in Antigen Receptor–Stimulated Human T Cells", *J. Immunol.,* 1991, 147, 3434–3440.

Mustelin et al., "Rapid Activation of the T–Cell Tyrosine Protein Kinase pp56$^{lck}$ by the CD45 Phosphotyrosine Phosphatase", *PNAS USA,* 1989, 86, 6302–6306.

Ostergaard et al., "Coclustering CD45 with CD4 or CD8 Alters the Phosphorylation and Kinase Activity of p56$^{lck}$",*J. Exp. Med.,* 1990, 172, 347–350.

Parnes, "Molecular Biology and Function of CD4 and CD8", *Adv. Immunol.,* 1989, 44, 265–311.

Raine et al., "On the Immunopathology of Plaque Development and Repair in Multiple Sclerosis", *J. Neuroimmunol.,* 1988, 20, 189–201.

Rivas et al., "CD4 Molecules are Associated with the Antigen Receptor Complex on Activated But Not Resting T Cells", *J. Immunol.,* 1988, 140, 2912–2918.

Shaw et al., "Short Related Sequences in the Cytoplasmic Domains of CD4 and CD8 Mediate Binding to the Amino–Terminal Domain of the p56$^{lck}$ Tyrosine Protein Kinase", *Mol. Cell. Biol.,* 1990, 10, 1853–1862.

Tite et al., "The Role of L3T4 in T Cell Activation: L3T4 May be Both an Ia–Binding Protein and a Receptor that Transduces a Negative Signal", *J. Mol. Cell. Immunol.,* 1986, 2, 179–189.

Turner et al., "Interaction of the Unique N–Terminal Region of Tyrosine Kinase p56$^{lck}$ with Cytoplasmic Domains of CD4 and CD8 is Mediated by Cysteine Motifs", *Cell,* 1990, 60, 755–765.

European Patent Office Supplementary European Search Report dated Jun. 12, 1997, 4 pages.

McDonnell et al., "Rational design of a peptide analog of the L3T4 CDR3–like region",*Immunomethods,* 1992, 1, 33–39.

Ohki et al., "Monoclonal antibodies to a CD4 peptide derivative which includes the region corresponding to an immunoglobulin CDR3: Evidence of the involvement of Pre–CDR3–Related Region in HIV–1 and Host Cell Interaction", *Mol. Immunol.,* 1992, 29(11), 1391–1400.

Deibler et al., "Isolation of Tryptic Peptides of Myelin Basic Protein by Reversed–Phase High–Performance Liquid Chromatography", *J. Chrom.,* 1985, 326, 433–442.

Mazerolles et al., "Immunosuppressive Properties of Synthetic Peptides Derived from CD4 and HLA–DR Antigens", *Cell,* 1988, 55, 497–504.

Zagury et al., "Critical sites: a semantic approach to protein sequences. Application to the HIV–1 envelope molecule", *Biomed & Pharmacother,* 1992, 46, 343–351.

Carr et al.,*J. Biol. Chem.,* 1989, 264(35) pp. 21286–21295.

COMPOUNDS THAT INHIBIT T CELL PROLIFERATION AND METHODS USING THE SAME

CROSS REFERENCE TO RELATED PATENT APPLICATIONS

This application is a continuation of U.S. Ser. No. 08/076,092 filed Jun. 11, 1993, which issued as U.S. Pat. No. 5,589,485, which is a continuation-in-part of U.S. application Ser. No. 07/977,692 filed Nov. 13, 1992, abandoned, which is incorporated herein by reference.

FIELD OF THE INVENTION

This invention relates to the field of immunology and in particular to the inhibition of undesired immune responses such as undesired activation of helper T cells.

BACKGROUND OF THE INVENTION

While normal T cells are an integral part of mammalian immune response, in some instances it is desirable to inhibit undesirable immune responses such as undesirable proliferation of T cells. For instance, autoimmune diseases are characterized as an immune reaction against "self" antigens. Autoimmune diseases include systemic lupus erythematosus (SLE), rheumatoid arthritis (RA) and multiple sclerosis (MS). SLE and RA have previously been treated with anti-inflammatory/immunosuppressive drugs such as steroids or anti-inflammatory drugs in combination with immunosuppressive drugs. No effective treatment has previously been found for MS although ACTH and other immunosuppressive drugs have elicited some degree of response when administered during relapse. Inhibition of the undesired immune response, such as those associated with RA, SLE and MS would be greatly desired to combat these conditions. T cells are an integral part of the immune response. Thus, treatment directed to inhibition of T cell proliferation would be greatly desired to treat such undesired immune responses.

T cells have also been implicated in graft rejection and graft versus host disease (GVHD). Administration of immunosuppression drugs such as cyclosporin is one method which is presently used in an attempt to combat graft rejection. GVHD has previously been treated by depleting T cells from the donor bone marrow. As in cases of autoimmune diseases, the undesired immune response may be targeted at the T cell level to reduce rejection of transplanted organs and prevent the recognition by transplanted T cells of a host organism as "foreign".

Furthermore, abnormal T cell growth associated with T cell leukemias may be treated by inhibiting the proliferation of T cells. Patients suffering from leukemias have low survival rates and are generally treated with chemotherapy. Methods directed toward the undesired proliferation of T cells may be useful for treatment of such leukemias.

There is a need for new compounds and methods for treating: autoimmune diseases including systemic lupus erythematosus (SLE), rheumatoid arthritis (RA) and multiple sclerosis (MS); graft rejection and graft versus host disease (GVHD) and T cell leukemias. There is a need for new compounds and methods directed to the inhibition of undesirable immune responses such as the undesired proliferation of T cells.

SUMMARY OF THE INVENTION

The present invention provides compounds which mimic the lateral surface of the glycoprotein CD4 conformationally. The compounds of the present invention are preferably 20 amino acids or less, more preferably 10–15 amino acids or less and comprise amino acid sequences derived from specific regions of CD4, are useful for modulating immune responses in mammals. The specific amino acid sequences comprise Ser-Gln-Lys, Ala-Ser-Gln, Asp-Gln-Lys, Gln-Lys-Glu, Lys-Glu-Glu, SEQ ID NO:30, Asn-Gln-Lys, Pro-Arg-Gly, Lys-Gln Ser, Gln-Ser-Ala, Lys-Gln-Asp, Glu-Lys-Gln, Glu-Glu-Lys, SEQ ID NO:66, Lys-Gln-Asn, or Gly-Arg-Pro.

The present invention relates to pharmaceutical compositions which comprise compounds that mimic the lateral surface of the glycoprotein CD4 conformationally. The compounds contained in the pharmaceutical compositions of the present invention are preferably 20 amino acids or less, more preferably 10–15 amino acids or less and comprise amino acid sequences derived from specific regions of CD4, are useful for modulating immune responses in mammals. The specific amino acid sequences comprise Ser-Gln-Lys, Ala-Ser-Gln, Asp-Gln-Lys, Gln-Lys-Glu, Lys-Glu-Glu, SEQ ID NO:30, Asn-Gln-Lys, Pro-Arg-Gly, Lys-Gln Ser, Gln-Ser-Ala, Lys-Gln-Asp, Glu-Lys-Gln, Glu-Glu-Lys, SEQ ID NO:66, Lys-Gln-Asn, or Gly-Arg-Pro.

The compounds of the present invention are useful for inhibiting the proliferation of T cells modulating immune responses in mammals. The present invention relates to methods of treating an individual suspected of suffering from a condition suffering from or being susceptible to a condition characterized by an undesired immune response, such as systemic lupus erythematosus, rheumatoid arthritis, multiple sclerosis, graft rejection, graft versus host disease and T cell leukemias; the method comprising the step of administering to the individual a pharmaceutical composition which comprises a compound that mimic the lateral surface of the glycoprotein CD4 conformationally. The compounds contained in the pharmaceutical compositions of the present invention are preferably 20 amino acids or less, more preferably 10–15 amino acids or less and comprise amino acid sequences derived from specific regions of CD4, are useful for modulating immune responses in mammals. The specific amino acid sequences comprise Ser-Gin-Lys, Ala-Ser-Gln, Asp-Gln-Lys, Gln-Lys-Glu, Lys-Glu-Glu, SEQ ID NO:30, Asn-Gln-Lys, Pro-Arg-Gly, Lys-Gln Ser, Gln-Ser-Ala, Lys-Gln-Asp, Glu-Lys-Gln, Glu-Glu-Lys, SEQ ID NO:66, Lys-Gln-Asn or Gly-Arg-Pro.

DETAILED DESCRIPTION OF THE INVENTION

Figure 1:
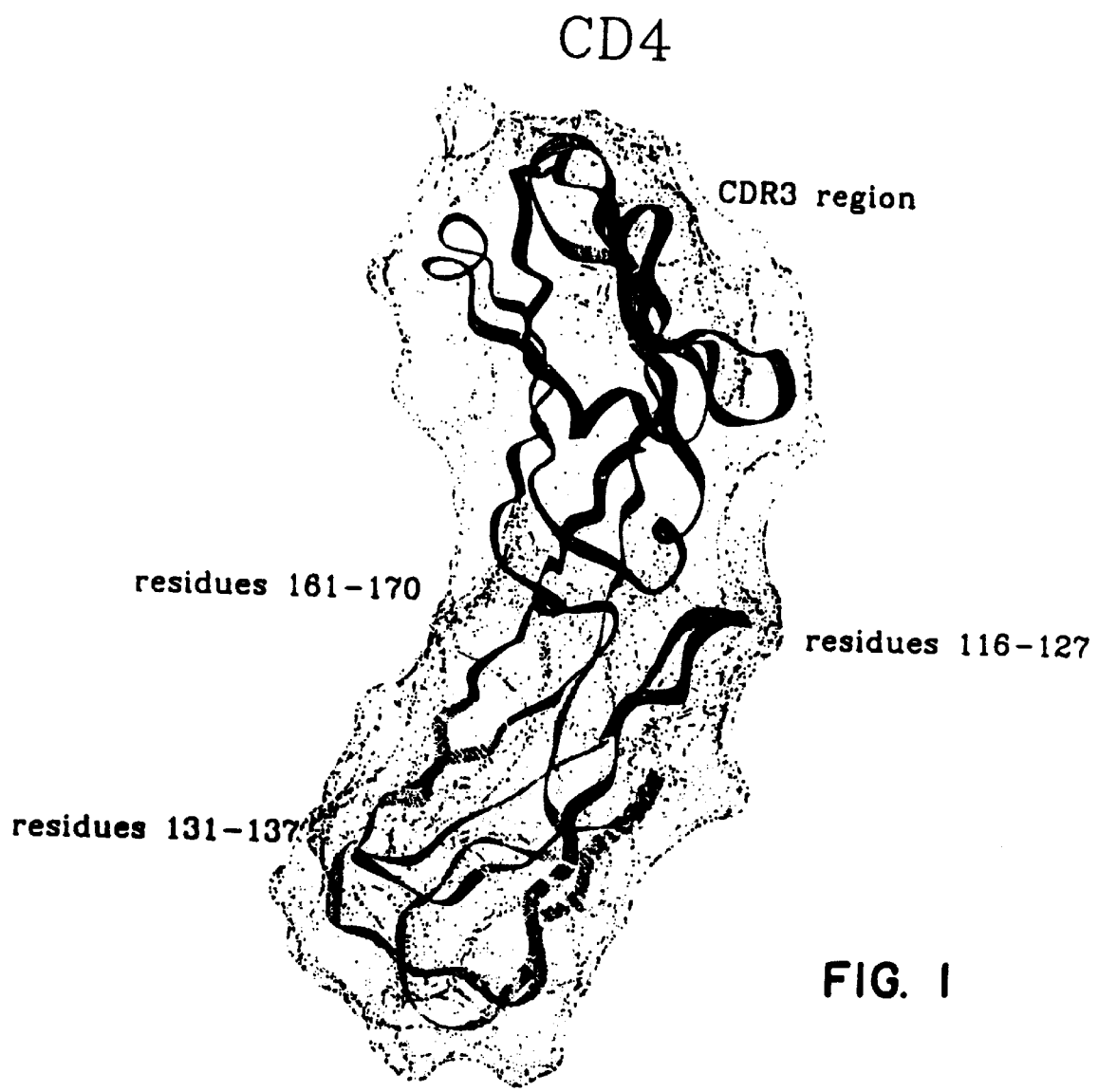
FIG. 1 shows a ribbon representation of the L3T4 protein model with the water accessible surface indicated.

CD4 is a cell surface glycoprotein that functions in synergy with the T cell receptor to generate the signals involved in T cell activation. Its expression correlates with the recognition of foreign antigen in association with self class II major histocompatibility complex (MHC) proteins on antigen presenting cells (Biddison et al., *J. Exp. Med.* 1982, 156, 1065–1071). Its expression is critical for regulating the positive and negative thymic selection processes that determine the T cell repertoire. CD4 has four external domains which show homology to members of the immunoglobulin superfamily; the amino terminal domain (D1), in particular, shows high homology to immunoglobulin Vκ chains (Parnes, *Adv. Immunology* 1989, 44, 265–311. The two amino terminal domains of CD4 (D1D2) have been implicated in augmenting the functional response of class II restricted T cells (Fleury et al., *Cell* 1991, 66, 1037–1049). A great deal of evidence suggests that CD4 acts as a coreceptor with the T cell receptor (TCR), binding a nonpolymorphic portion of the class II MHC protein while the TCR provides specificity binding to antigen and a polymorphic portion of the MHC (Gay et al., *Nature* 1987, 328, 626–629). It is widely believed that CD4 enhances the overall avidity of this interaction to allow recognition of foreign antigen at physiological concentrations.

The presence of CD4 as a coreceptor can potentiate the T cell response as much as 300-fold (Janeway, *Sem. Immunology* 1991, 3, 153–160). Several studies have indicated that the major contribution of CD4 is as a signal transduction molecule, rather than as an affinity enhancer. Indeed, in several direct binding studies the presence of CD4 had no affect of affinity of MHC for the T cell (Matsui et al., *Science* 1991, 254, 1788–1791). CD4 is intimately involved in the TCR mediated signal transduction pathway leading to the activation of T helper cells. Numerous studies have shown that monoclonal antibodies specific for CD4 can inhibit T cell activation induced by lectin or antibody directed against the CD3-TCR complex, despite the absence of class II ligand in these systems (Bank and Chess, *J. Exp. Med.* 1985, 162, 1294–1303; Tite et al., *J. Mol. Cell. Immunol.* 1986, 2, 179–189). These data have led some to hypothesize that CD4 is capable of delivering a negative signal. Other data clearly indicate that CD4 can deliver positive signals, its inclusion in the signalling complex lowering the threshold for activation two to three orders of magnitude (Ledbetter et al., *Eur. J. Immunology* 1988, 18, 525–532).

The cytoplasmic domain of CD4 is noncovalently associated with $p56^{lck}$, a src-related tyrosine kinase (Barber et al., *PNAS USA* 1989, 86, 3277–3281). Site-directed mutagenesis of the cytoplasmic tail defines a double cysteine motif that is required for association with $p56^{lck}$ (Shaw et al., *Molec. Cell. Biol.* 1990, 10, 1853–1862; Turner et al., *Cell* 1990, 60, 755–765). Transgenic mice deficient for $p56^{lck}$ fail to develop any T cells (Tak Mak, personal communication), and CD4 mutants lacking the cytoplasmic domain are deficient in T cell activation (Glaichenhaus et al., *Cell* 1991, 64, 511–520), strongly suggesting that the triggering of $p56^{lck}$ is involved in T cell activation. As with other src-family members possessing a conserved carboxyl-terminal tyrosine kinase domain, association with distinct cellular receptors occurs through unique amino-termini; in this manner, extracellular ligands may control the tyrosine kinase. Antibody cross-linking of CD4 has been demonstrated to result in phosphorylation of the ζ chain (and possibly the Δ and ε chains) of the CD3-TCR complex on tyrosine residues (Barber et al., 1989, supra). The net result of the CD3 phosphorylation may be to alter the intermolecular associations within the CD3-TCR complex, leading to the cascade of events linked to T cell activation.

In addition to its interactions with molecules on a different cell, CD4 is also involved in interactions with other T cell surface molecules, presumably in its capacity as a signal transduction molecule. A physical association between CD4 and the CD3/TCR complex has been demonstrated by several groups. Janeway et al., *CSH Symp. Quant. Biol.* 1989, LIV, 657–666, showed that monoclonal anti-CD4 could inhibit activation of T cell clones in response to monoclonal antibodies directed against certain epitopes of the TCR but not others. Further, high-potency anti-TCR caused cocapping and comodulation of TCR with CD4, while lower potency (20–500 fold) anti-TCR could not. Others have demonstrated that the physical association of CD4 with CD3/TCR occurs efficiently only on activated, and not resting T cells (Mittler et al., *PNAS USA* 1989, 86, 8531–8535; Rivas et al., *J. Immunology* 1988, 140, 2912–2918). A physical association has also been shown to occur between CD4 and CD45. CD45 is a membrane bound protein tyrosine phosphatase (PTPase) expressed on all cells of hemopoietic origin. CD45-negative T cell variants are incapable of T cell activation through TCR-mediated events but can be stimulated via IL-2 mediated pathways (Matthews et al., *CSH Symp. Quant. Biol.* 1989, LIV, 675–682). It has been reported that CD45 directly dephosphorylates p56$^{lck}$ in in vitro assays, leading to dramatic enhancement of the p56$^{lck}$ kinase activity. (Mustelin et al., *PNAS USA* 1989, 86, 6302–6306). Fluorescent resonance energy transfer analysis was used to demonstrate a close physical apposition of the two molecules on the surface of activated but not resting T cells (Mittler et al., *J. Immunology* 1991, 147, 3434–3440). Functionally, coclustering of CD45 with CD4 results in an altered state of p56$^{lck}$ phosphorylation and a concomitant increase in kinase activity (Ostergaard and Trowbridge, *J. Exp. Med.* 1990, 172, 347–350). Moreover, Dianzani et al., *Eur. J. Immunology* 1990, 20, 2249–2257, have demonstrated a correlation between physical association between CD4 and different CD45 isoforms and the state of immunological memory. The CD4 protein, and particularly the lateral surface, is believed to be involved in the regulation of a complex signalling pathway that ultimately leads to stimulation of T cell proliferation.

The nucleotides sequence encoding CD4 protein and the amino acid sequence of the CD4 protein are well known. As used herein, the numbering system used to refer to specific amino acid residues of CD4 is the standard numbering system well known and regularly used by those having ordinary skill in the art. See, for example, Maddon, P. et al. (1985) *CELL* 42:93–104, Maddon, P. et al. (1986) *CELL* 47:333–348, and Hussey, R. E., (1988) *Nature* 331:78–81, each of which is incorporated herein by reference.

The present invention provides peptides useful for and method of modulating immune responses in mammals. Peptides are provided comprising an amino acid sequence corresponding to at least a portion of one the five distinct regions of CD4 which are referred to herein as: 1) CDR1; 2) CDR3; 3) 127; 4) 147; and 5) 161; and are preferably 15 amino acids or less. The peptides of the invention have a restricted conformation and the ability to modulate immune response by intervening in intermolecular interactions between proteins.

The regions were determined based upon the crystal structure of the glycoprotein CD4. In particular, the lateral surface of CD4, which is presented by the D1–D2 domains of the CD4 protein and believed to be involved in protein-protein interactions, was modeled and used as a template for the design of conformationally restricted peptides. FIG. 1 depicts the D1–D2 domains of CD4.

Each of the five distinct regions of CD4 identified above is formed from a specific sequence of amino acids that comprises essential amino acids plus flanking sequences. As they exist in CD4, these regions form surfaces which are each capable of interacting with other molecules. Compounds of the invention are designed using one or more of these distinct regions of CD4 as models. The compounds of the invention provide a similar surface as that of at least one of the five identified regions of CD4. Accordingly, the compounds of the invention are able to mimic the intermolecular interactions of the at least one of the five regions of CD4. The compounds of the invention are capable of inhibiting a T cell proliferation and thereby are useful in the treatment and prevention of disorders and conditions characterized by undesirable T cell proliferation.

As used herein, the term "compound" refers to molecules which include peptides and non-peptides including, but not limited to molecules which comprise amino acid residues joined by at least some non-peptidyl bonds. The term "peptide" as used herein refers to polypeptides formed from naturally occurring amino acid subunits joined by native peptide bonds. Thus, this term effectively refers to naturally occurring subunits or their close homologs. The term amino acid may also refer to moieties which have portions similar to naturally occurring peptides but which have non-naturally occurring portions. Thus, peptides may have altered amino acids or linkages. Peptides may also comprise other modifications consistent with the spirit of this invention. Such peptides are best described as being functionally interchangeable yet structurally distinct from natural peptides. As used herein, the terms "compounds" and "peptides" are used interchangeably.

Compounds of the invention include fragments of CD4 which comprise at least one of the five identified regions of CD4, which present a physical surface which mimics the surface of at least one of the five identified regions of CD4 and which are capable of inhibiting T cell proliferation. Peptides of the present invention may range from about 3 to about 100 amino acids in length. In some embodiments of the present invention, peptides of the present invention are from about 3 to about 50 amino acids in length. In preferred embodiments of the present invention peptides of the present invention are from about 3 to about 20 amino acids in length, more preferably about 3–15 amino acids in length. It is preferred that peptides are as small as possible. In some embodiments, the peptides are about 3–10 amino acids. Amino acid sequences of peptides of the present invention comprise a portion of a CD4 region that is at least 2–7 amino acids.

Because the tertiary structure of a peptide does not necessarily imitate that of its parent protein, it was necessary to covalently close the peptide analogs to force a desired folding pattern. Rather than being a rigid isosteric analogs, peptides were restricted to predicted conformational repertoires such that it would overlap the shape and movement of the native protein. Amino- and carboxy- terminal cysteines and intramolecular disulfides were used in some embodiments of the present invention to close peptides and limit the potential solution conformers. Additional means of circularizing peptides are also well known.

Methods employed to circularize peptides into functional conformational include incorporating proline at the terminal into the amino acid sequence. In some embodiments, the amino acid sequence proline-glycine-proline (PGP) may be used to impose a constrained turn in the peptide analog as described in Example 1. Critical to the PGP turn motif is the rigid constraints that the amino acid proline can impose on the backbone of a peptide chain. The side chain of proline, a cyclic five member ring (prolidyl ring), is bonded covalently to the nitrogen atom of the peptide group, therefore dramatically limiting rotation about the N-Cα (phi) bond of the backbone, with the adjacent peptide bond more likely to adopt a cis configuration. In contrast, the inherent flexibility of the glycine residue allows for the occurrence of the tight turn, strongly induced by the rigid neighboring prolines, without the steric side-chain constraints other amino acids would experience. Computer simulation of energy-dependent motion and molecular mechanics calculations were performed on peptides modelled in bulk aqueous solution to predict those analogs whose conformational folding repertoire would overlap that of the native protein.

In the preferred embodiments of the invention, peptides consist of 15 amino acid residues or less and are circularized or otherwise conformationally restricted in order to provide surfaces which mimic surfaces of the CD4 molecule. The peptides of the invention comprise at least the essential amino acid sequences from at least one of the identified regions of CD4. They may additionally comprise the CD4 sequences that flank the essential sequences in the CD4 molecule or non-CD4 sequences or a combination of CD4 and non-CD4 sequences. Further, the peptides may comprise non-CD4 residues required to achieve proper three dimensional conformation including residues which facilitate circularization.

The following provides a description of each of the five distinct regions of CD4 which have been identified as being implicated in a signalling process associated with T cell proliferation. Included is the identification of the amino acid sequences that make up each region and the essential amino acid sequences of each region. Compounds of the invention include the essential sequences and preferably some or all of the flanking sequences. As noted above, compounds may contain only CD4 sequences or a combination of CD4 and non-CD4 sequences. Compounds of the invention mimic the region of CD4 which they conformationally resemble. Accordingly, they can interact with other proteins that would otherwise interact with CD4 itself including those proteins involved in signaling stimulation of T cell proliferation. Compounds that comprise amino acid sequence from one of the five distinct portions of CD4 may be used to modulate immune responses and inhibit T cell proliferation.

The CDR1 region of CD4 includes amino acids 17–22 (SEQ ID NO:15) and the essential amino acids of CDR1 are amino acids 19–21 (Ser Gln Lys) and 18–20 (Ala Ser Gln). CDR1 peptides comprise amino acids 19–21 (Ser Gln Lys) of CD4 and may comprise the additional flanking sequences from CD4. In some embodiments of the invention, peptides comprise amino acids 17–22 (SEQ ID NO:15), 17–21 (SEQ ID NO:16), 18–21 (SEQ ID NO:17), 18–22 (SEQ ID NO:18) or 19–22 (SEQ ID NO:19). Some embodiments of the invention comprise additional CD4 or non-CD4 flanking sequences.

The CDR3 region of CD4 includes amino acids 87–93 (SEQ ID NO:20) and the essential amino acids of CDR3 are amino acids 88–90 (Asp Gln Lys), 89–91 (Gln Lys Glu) or 90–92 (Lys Glu Glu). CDR3 peptides comprise amino acids 88–90 (Asp Gln Lys), 89–91 (Gln Lys Glu) or 90–92 (Lys Glu Glu) of CD4. In some embodiments of the invention, peptides comprise amino acids 87–93 (SEQ ID NO:20) 87–90 (SEQ ID NO:21), 87–91 (SEQ ID NO:22), 87–92 (SEQ ID NO:23), 88–91 (SEQ ID NO:24), 88–92 (SEQ ID NO:25), 88–93 (SEQ ID NO:26), 89–92 (SEQ ID NO:27), 89–93 (SEQ ID NO:28) or 90–93 (SEQ ID NO:29). Some embodiments of the invention comprise additional CD4 or non-CD4 flanking sequences.

The 127 region of CD4 includes amino acids 117–128 (SEQ ID NO:58) and essential amino acids are amino acids 120–124 (SEQ ID NO:30). 127 peptides comprise amino acids 120–124 (SEQ ID NO:30) of CD4. In some embodiments of the invention, peptides comprise amino acids 117–128 (SEQ ID NO:58), 117–124 (SEQ ID NO:31), 117–125 (SEQ ID NO:32), 118–124 (SEQ ID NO:33), 118–125 (SEQ ID NO:34), 118–126 (SEQ ID NO:35), 119–124 (SEQ ID NO:36), 119–125 (SEQ ID NO:37), 119–126 (SEQ ID NO:38), 120–125 (SEQ ID NO:39), 120–126 (SEQ ID NO:40), 117–127 (SEQ ID NO:59), 118–127 (SEQ ID NO:60), 118–128 (SEQ ID NO:61), 119–127 (SEQ ID NO:62), 119–128 (SEQ ID NO:63), 120–127 (SEQ ID NO:64) or 120–128 (SEQ ID NO:65). Some embodiments of the invention comprise additional CD4 or non-CD4 flanking sequences.

The 147 region of CD4 includes amino acids 158–171 and essential amino acids are amino acids 164–166 (Asn Gln Lys). 147 peptides comprise at least amino acids 164–166 (Asn Gln Lys) of CD4. In some embodiments of the invention, peptides comprise amino acids 163–166 (SEQ ID NO:41). Some embodiments of the invention comprise additional CD4 or non-CD4 flanking sequences.

The 161 region of CD4 includes amino acids 130–138 (SEQ ID NO:42) and essential amino acids are amino acids 133–135 (Pro Arg Gly). 161 peptides comprise at least amino acids 133–135 (Pro Arg Gly) of CD4. In some embodiments of the invention, peptides comprise amino acids 130–138 (SEQ ID NO:42), 130–135 (SEQ ID NO:43), 130–136 (SEQ ID NO:44), 130–137 (SEQ ID NO:45), 131–135 (SEQ ID NO:46), 131–136 (SEQ ID NO:47), 131–137 (SEQ ID NO:48), 131–138 (SEQ ID NO:49), 132–135 (SEQ ID NO:50), 132–136 (SEQ ID NO:51), 132–137 (SEQ ID NO:52), 132–138 (SEQ ID NO:53), 133–136 (SEQ ID NO:54), 133–137 (SEQ ID NO:55) or 133–138 (SEQ ID NO:56). Some embodiments of the invention comprise additional CD4 or non-CD4 flanking sequences.

It is possible to construct compounds of the invention which comprise essential amino acids from more than one of the five distinct regions of CD4. For example, the three dimensional structure of CD4 regions CDR1 and CDR3 occur in close proximity to each other. The CDR1 region of CD4 includes amino acids 17–22 (SEQ ID NO:15) and the essential amino acids of CDR1 are amino acids 19–21 (Ser Gln Lys). The CDR3 region of CD4 includes amino acids 87–93 (SEQ ID NO:20) and the essential amino acids of CDR3 are amino acids 88–90 (Asp Gln Lys), 89–91 (Gln Lys Glu) or 90–92 (Lys Glu Glu). In one embodiment, compounds may be constructed which comprise sequences from both regions such that the compound may mimic the surface produced by the two regions on CD4. Such compounds comprise amino acid sequences from both regions and may optionally comprise amino acid residues between the two region-derived sequences. As in the case of designing compounds modelled after single regions, conformational considerations are most important in defining both CD4 and non-CD4 residues to be included in the compound. In some embodiments, compounds comprise CD4 amino acids 18–20 (Ala Ser Gln) and 88–90 (Asp Gln Lys). Additionally, compounds may comprise cysteines. Furthermore, in some embodiments, compounds have proline and alanine between the two region-derived sequences. One embodiment contains the sequence Cys Gln Ser Ala Pro Ala Asp Gln Lys Cys (SEQ ID NO:57) circularized by disulfide bonds between the cysteines.

The amino acid sequences described herein may be constructed to proceed in sequence from the amino terminus to carboxy terminus or from the carboxy terminus to the amino terminus. When the sequence proceeds from the amino terminus to carboxy terminus, it is usually constructed of L amino acids. When D amino acids are used to construct the compound, the sequence is usually reversed from the order it occurs in CD4 and it therefore proceeds from the carboxy terminus to the amino terminus. It is intended that each of the amino acid sequences described herein, including SEQ ID NOS:1–65, are intended to describe amino acid sequences proceeding from the amino terminus to carboxy terminus and amino acid sequences proceeding from the carboxy terminus to the amino terminus.

Compounds which mimic the lateral surface of the CD4 protein may be used to treat undesired immune responses in humans. For example, autoimmune diseases such as rheumatoid arthritis, multiple sclerosis, and SLE may be treated by administration of compounds of the present invention to a patient suffering from such an autoimmune disease in order to inhibit this undesired immune response. Inhibition of T cell proliferation is one route by which an undesired immune response may be inhibited. Compounds of the present invention are also useful for treatment of patients suffering from graft rejection and graft versus host disease. By administering compounds of the present invention to a patient which has received transplanted tissues, organs, bone marrow, etc., rejection of the foreign material may be avoided by inhibiting an undesired immune response which may cause rejection. For example, compounds of the present invention may be administered to patients suffering from graft versus host disease to inhibit the "self" recognizing immune response. Administration of compounds may inhibit T cell proliferation in some embodiments of the present invention. In addition, in preparation for a transplant procedure, compounds of the present invention may be administered to a patient in order to reduce the likelihood of an undesired immune response which may result in rejection of the transplant. Compounds of the present invention may also be administered to treat abnormal T cell growth such as T cell growth associated with T cell leukemia. In accordance with methods of the present invention, compounds are administered to a patient suffering from such abnormal T cell growth to inhibit the abnormal proliferation of T cells. In some preferred embodiments of the present invention peptides set forth in Table I are provided.

The peptides of the present invention may be prepared by any of the following known techniques. Conveniently, the peptides may be prepared using the solid-phase synthetic technique initially described by Merrifield, in *J. Am. Chem. Soc.*, 15:2149–2154 (1963). Other peptide synthesis techniques may be found, for example, in M. Bodanszky et al., (1976) *Peptide Synthesis*, John Wiley & Sons, 2d Ed.; Kent and Clark-Lewis in *Synthetic Peptides in Biology and Medicine*, p. 295–358, eds. Alitalo, K., et al. Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984). The synthesis of peptides by solution methods may also be used, as described in *The Proteins*, Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973).

In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

The present peptides may also be prepared by recombinant DNA techniques, although such methods are not preferred because of the need for purification and subsequent chemical modifications to conformationally restrain the peptides.

In addition to peptides which comprise L amino acids, pharmaceutical compositions according to the present invention may comprise peptides made up of D amino acids. Because most enzymes involved in degradation recognize a tetrahedral alpha-carbon, the D-amino acids were utilized in order to avoid enzyme recognition and subsequent cleavage. Computer studies indicate that the same folded presentation of the peptide is accomplished by reversing the amino acid sequence, employing D-amino acids. Thus, peptides comprised of D amino acids are less susceptible to degradation. In some embodiments of the present invention, compounds comprising D amino acids are provided which comprise the same amino acid sequences as those presented throughout this disclosure but in reverse order, i.e. from the carboxy terminus to the amino terminus. Thus, the present disclosure is meant to specifically encompass each of the sequences set out herein as additionally describing peptides from the carboxy terminus to the amino terminus which comprising D amino acids.

Conservative substitutions in the amino acid sequence may be made. Those having ordinary skill in the art can readily design CD4 analogs with conservative substitutions for amino acids. For example, following what are referred to as Dayhof's rules for amino acid substitution (Dayhof, M. D. (1978) *Nat. Biomed. Res. Found.*, Washington, D.C. Vol. 5, supp. 3), amino acid residues in a peptide sequence may be substituted with comparable amino acid residues. Such substitutions are well known and are based the upon charge and structural characteristics of each amino acid.

Synthesized peptides which contain portions of a CD4 region may be circularized in order to mimic the geometry of those portions as they occur in CD4. Circularization may be facilitated by disulfide bridges between cysteine residues. Cysteine residues may be included in positions on the peptide which flank the portions of the peptide which are derived from a CD4 region. Cysteine residues within the portion of a peptide derived from CD4 may be deleted and/or conservatively substituted to eliminate the formation of disulfide bridges involving such residues. Alternatively, the peptides may be circularized by means of covalent bonds, such as amide bonds, between amino acid residues of the peptide such as those at or near the amino and carboxy termini.

The present invention provides compounds that comprise peptides which contain at least a portion of the amino acid sequence of CD4. The portion of CD4 may be from 2–100 amino acids. In preferred embodiments, the portion of CD4 may be from 2–20, more preferably 2–15 amino acids. Non-CD4 amino acid sequences are provided in some embodiments. In other embodiments, the peptide contains only CD4 amino acid sequences. At least 10% of the amino acid sequence of the peptides of the present invention are preferably derived from the portion of CD4. In some embodiments, it is preferred that greater than about 20–25% of the amino acid sequence of the peptides of the present invention are preferably derived from the portion of the CD4, more preferably 30–40% and more preferably greater than 50%. In some embodiments, the percentage of amino acid sequence of the peptides of the present invention derived from the portion of the CD4 approaches about 60% or about 75% or more.

To determine whether a peptide having the structural properties defined herein is useful in the pharmaceutical compositions and methods of the present invention, routine assays may be performed using such peptides to determine whether the peptides possess the requisite activity; i.e. whether the peptide can inhibit T cell proliferation. The peptides ability to inhibit T cell proliferation may be determined by observing its activity in T cell proliferation assays. T cell proliferation assays are well known to those having ordinary skill in the art and may be constructed from readily available starting materials. Examples 5–16, set out below, provide description of assays that can be used to determine whether or not a compound has the requisite activity.

Peptides having the structural characteristics described above may be synthesized routinely. Such peptides may be tested using standard assays to determine if they can be used in pharmaceutical compositions and methods according to the present invention.

The present invention provides pharmaceutical compositions that comprise the compounds of the invention and pharmaceutically acceptable carriers or diluents. The pharmaceutical composition of the present invention may be formulated by one having ordinary skill in the art with compositions selected depending upon the chosen mode of administration. Suitable pharmaceutical carriers are described in Remington's Pharmaceutical Sciences, A. Osol, a standard reference text in this field. In carrying out methods of the present invention, peptides of the present invention can be used alone or in combination with other diagnostic, therapeutic or additional agents. Such additional agents include excipients such as flavoring, coloring, stabilizing agents, thickening materials, osmotic agents and antibacterial agents. Such agents may enhance the peptide's use in vitro, the stability of the composition during storage, or other properties important to achieving optimal effectiveness.

For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the active agent to reach the targeted cells. Because peptides are subject to being digested when administered orally, parenteral administration, i.e., intravenous, subcutaneous, intramuscular, would ordinarily be used to optimize absorption. Intravenous administration may be accomplished with the aid of an infusion pump. The pharmaceutical compositions of the present invention may be formulated as an emulsion. Alternatively, they may be formulated as aerosol medicaments for intranasal or inhalation administration. In some cases, topical administration may be desirable.

The dosage administered varies depending upon factors such as: pharmacodynamic characteristics; its mode and route of administration; age, health, and weight of the recipient; nature and extent of symptoms; kind of concurrent treatment; and frequency of treatment. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

Depending upon the disease or disorder to be treated, the pharmaceutical compositions of the present invention may be formulated and administered to most effectively. Modes of administration will be apparent to one skilled in the art in view of the present disclosure.

The following examples are illustrative but are not meant to be limiting of the present invention.

EXAMPLES

Example 1

Molecular Modeling

A molecular model of the mouse CD4 protein (L3T4) was developed from the high resolution crystal structure of human CD4 (Brookhaven code: 1CD4). Computer algorithms were used to simulate energy dependent motion (molecular dynamics) and perform molecular mechanics calculations. This work was performed using the computational chemistry package supplied by Molecular Simulations/Polygen Inc. (Pasadena, Calif.) and a Silicon Graphics (Mountain View, Calif.) Power Series 4D/480 parallel process computer. A description of the modeling package has been described previously by Jameson, B. A., Nature 1989, 341, 465.

L3T4 Protein

In general, the amino acid compositions and functional properties of the Ig-superfamily are highly diverse; however, the backbone folding patterns are remarkably conserved, primarily due to the conservation of relatively few key residues that maintain structure. These key structural motifs were maximized by comparing and aligning unknown proteins to known structures. Key positions are more heavily weighted and a structurally similar matrix is used that penalizes less for changes that involve either chemically homologous changes or residues with similar structural properties. After maximizing for structural homology, the amino acid composition of the L3T4 protein was superimposed on the backbone of the crystal structure of human CD4, and the newly incorporated side-chains were allowed to equilibrate themselves in successive series of energy minimization calculations. Because the Ig fold consists of a series of well defined series of paired antiparallel beta strands, these paired structures were initially treated as elementary units. In the first series of dynamic calculations, the anti-parallel strands were allowed to realign themselves; subsequently paired strands were allowed to interact with neighboring strands and finally, the entire structure was allowed to conformationally equilibrate. All of the calculations were performed in the presence of bulk aqueous solvent. The resulting structure was stable in long dynamics runs (100 picoseconds) and is stable to energy perturbations such as heating and cooling. The structure was then used as a template for the design of functional peptide analogs.

Peptides

Immunoglobulin variable domains contact antigen utilizing a protein surface created by the presentation of three substructures referred to as complementary determining regions (CDR). It was hypothesized that L3T4, as a member of the Ig superfamily, might also utilize CDR-like regions to mediate protein-protein interactions. Rationally-designed chemical constraints such as amino and carboxyl-terminal cysteines, and an intramolecular disulfide enrichment procedure, to covalently close the peptide and limit the potential source of conformers, were introduced into some peptide analog in order to force a desired folding pattern.

Peptide 1

The CDR3-like region of L3T4 domain 1 was chosen as one candidate for design of peptide mimics because it consists of two antiparallel beta strands connected by a reverse turn, and its folding is somewhat independent from the rest of the structure.

From analysis of the predicted protein structure it was predicted that only a portion of the CDR3-like region (residues 86–97) was exposed to solvent and available for binding, namely the carboxyl-terminal beta strand and a portion of the reverse turn. Thus, a peptide was designed to maintain these structures while keeping the native sequence intact. A turn motif was used that would force the formation of an antiparallel beta stranded stem loop structure, stabilizing the presentation of the 86–93 region in a CDR3-like conformation. The amino acid sequence proline-glycine-proline (PGP) was used to impose a constrained turn in the peptide analog. Critical to the PGP turn motif is the rigid constraints that the amino acid proline can impose on the backbone of a peptide chain. The side chain of proline, a cyclic five member ring (prolidyl ring), was bonded covalently to the nitrogen atom of the peptide group, therefore dramatically limiting rotation about the N-Cα (phi) bond of the backbone, with the adjacent peptide bond more likely to adopt a cis configuration. In contrast, the inherent flexibility of the glycine residue allows for the occurrence of the tight turn, strongly induced by the rigid neighboring prolines, without the steric side-chain constraints other amino acids would experience. Computer simulation of energy-dependent motion and molecular mechanics calculations were performed on peptides modelled in bulk aqueous solution to predict those analogs whose conformational folding repertoire would overlap that of the native protein. The amino acid sequence of Peptide 1 is shown as SEQ ID NO:1.

Peptide 2

Like SEQ ID NO:1, PEPTIDE 2 (SEQ ID NO:13, mCDR3 scramble) was derived from the CDR3-like region, however the sequence was scrambled.

Peptide 3

PEPTIDE 3 (SEQ ID NO:3, hPGPtide) was derived from the CDR3-like region of human CD4. SEQ ID NO:3 possesses the same PGP turn motif present in SEQ ID NO:1.

Peptide 4

PEPTIDE 4 (SEQ ID NO:4, h158-171 C—C) represents one of the middle corners of the lateral surface (derived from the D2 domain of human CD4 protein). An obvious topological protrusion from the lateral surface occurs at a middle edge centered around residue 165 of the CD4 protein. The peptide was designed to mimic the presentation of the surface exposed amino acids Leu(162), Gln(163), Asn(164), Gln(165), Lys(166), Lys(167), and Glu(169). Computer simulation of molecular dynamics and mechanics were used to screen potential peptides sequences to arrive at a sequence incorporating residues 158 through 171, where Phe170 was replaced with a cysteine in order to cyclize the peptide and recreate a portion of the surface found in the native protein.

Peptide 5

PEPTIDE 5 (SEQ ID NO:5, h117-126 linear) represents the side opposite PEPTIDE 4 (SEQ ID NO:4) on the middle of the lateral surface of the D1–D2 domain of CD4, centered around residue 122. Because of the extensive prolines found naturally within this sequence, conformational restraints were unnecessary.

Peptide 6

PEPTIDE 6 (SEQ ID NO:6, h130-138 C—C) represents the bottom-most portion of the lateral surface of the D1–D2 domain of CD4, centered around residue 134. It was attempted to correctly position the surface exposed residues Arg(131), Arg(134), Lys(136), and Asn(137). In order to avoid torsional strain, the first artificially introduced cysteine was a d-amino acid.

Peptide 7

PEPTIDE 7 (SEQ ID NO:7, m86-104 C—C) represents a region of the L3T4 CDR3 region incorporating cysteines at the terminal ends to achieve folding.

Peptide 8

PEPTIDE 8 (SEQ ID NO:8, m86-104 linear) is identical in sequence and size to PEPTIDE 7 (SEQ ID NO:7) but lacks the restraining carboxyl terminal cysteine. Unlike PEPTIDE 7 (SEQ ID NO:7) the linear peptide cannot cyclize because phenylalanine 104 was not replaced with a cysteine.

Peptide 9

PEPTIDE 9 (SEQ ID NO:9, m86-104 scramble) retained the same amino acid composition as PEPTIDE 7 (SEQ ID NO:7) including cysteines at either end, but had its sequence order was randomized. A patch of negatively charged amino acids was retained in this version to rule out the possibility that the negative patch present in PEPTIDE 7 (SEQ ID NO:7) was influenced any cellular reactions.

Peptide 10

PEPTIDE 10 (SEQ ID NO:10, m86-103 C—C) was truncated by one amino acid relative to the authentic CDR3 analog. This peptide was intentionally designed to have an inappropriate conformational repertoire.

Example 2

Peptide Synthesis

Peptides were synthesized on an Applied Biosystem (Foster City, Calif.) 430A fully automated peptide synthesizer according to methods of Jameson et al., *Science* 1988, 240, 1335. The peptides containing internal cysteine residues were refolded and oxidized by dissolving them at 100 μg/ml in 0.1 M NH$_4$HCO$_3$ and stirring overnight exposed to air at 23° C. The peptides show greater than 95% intramolecular disulfide bonding at the end of this procedure as monitored by Ellmans reagents, HPLC analysis and gel filtration. Peptides were lyophilized, resuspended in complete medium and filtered through a 0.22 μ filter prior to use in biological assays. The sequences of the synthesized peptides are set forth in Table I.

TABLE I

| DESIGNATION | SEQUENCE | SEQ ID NO |
|---|---|---|
| mPGPtide (mouse CDR3 analog) | CELENRKEEPGPC | 1 |
| h84–101 C-C (84–101 cys) | CEVEDQKEEVQLLVFGLC | 2 |
| hPGPtide (human CDR3 analog) | CEVEDQKEEPGPC | 3 |
| h158–171 C-C (147) | TCTNLQNQKKVECK | 4 |
| h117–126 linear (127) | LESPPGSSPSV | 5 |
| h130–138 C-C (161) | C*RSPRGKNC | 6 |
| m86–104 C-C | CELENRKEEVEWVFKVTC | 7 |
| m86–104 linear | CELENRKEEVEWVFKVTF | 8 |
| m86–104 scramble | CWKVFTLEVVEKERNEELC | 9 |
| m86–103 C-C | CELENRKEEVEWVFKVC | 10 |
| unrelated control (control) | HYKLSQRGYEWDAGDGC | 11 |
| h84–101 linear (84–101 linear) | CEVEDQKEEVQLLVFGLT | 12 |
| h84–101 scramble (scramble) | CLLVFEVEDQKEEVQGLC | 13 |
| h18–40 linear (CD4 18–40) | ASQKKSIQFHWLNSNQILIL GNQ | 14 |

*indicates D-amino acid

Example 3
NMR Measurements and Peptide Modelling 5 mg of peptide was dissolved in 450 μl of 10 mM potassium phosphate. The pH of the solution was adjusted to 6.0, and 50 μl of deuterated trifluoroethanol was added. The resulting solution was transferred to a 5 mm NMR tube.

All $^1$H NMR spectra were recorded on a Bruker (Billerica, Mass.) AMX600 spectrometer at 278K. All spectra were acquired at 5° C. Spin specific assignments were obtained using the following 2D NMR experiments, double quantum filtered correlated spectroscopy (DQF-COSY) and totally correlated spectroscopy (TOCSY). Bax and Davis, *J. Mag. Reson.* 1985, 65, 355. NOESY experiments were used to make sequential assignments and to detect secondary structure. Kumar et al., *Biochem. Biophys. Res. Commun.* 1980, 95, 1. A spectral width of 600 Hz was used in both dimensions and 16 and 64 scans were recorded per t1 increment for the TOCSY and NOESY, respectively. The mixing time was 70 ms for TOCSY and 400 ms for NOESY spectra.

The NOE derived distance constraints were incorporated into the standard force field used in the modeling program Discover (Biosym Technologies, San Diego, Calif.). The peptide model was obtained using a simulated annealing procedure. An extended conformation of the peptide in bulk water was subjected to high temperature (900K) molecular dynamics (MD), annealed by performing MD at 300K and finally minimized to an average derivative of 0.01 kcal/mol-angstrom.

Figure 9B:
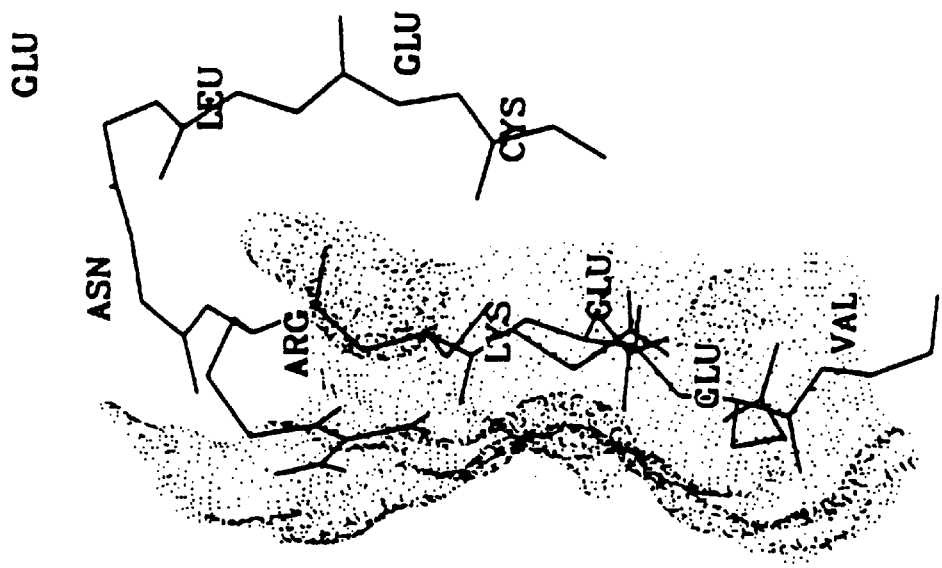
FIGS. 9A–9B is a comparison of the water accessible surface of the CDR3 like region of L3T4 based on the protein model (FIG. 9B) and the water accessible surface of the putative binding region of SEQ ID NO:1 based on NMR analysis (FIG. 9A).
Figure 9A:
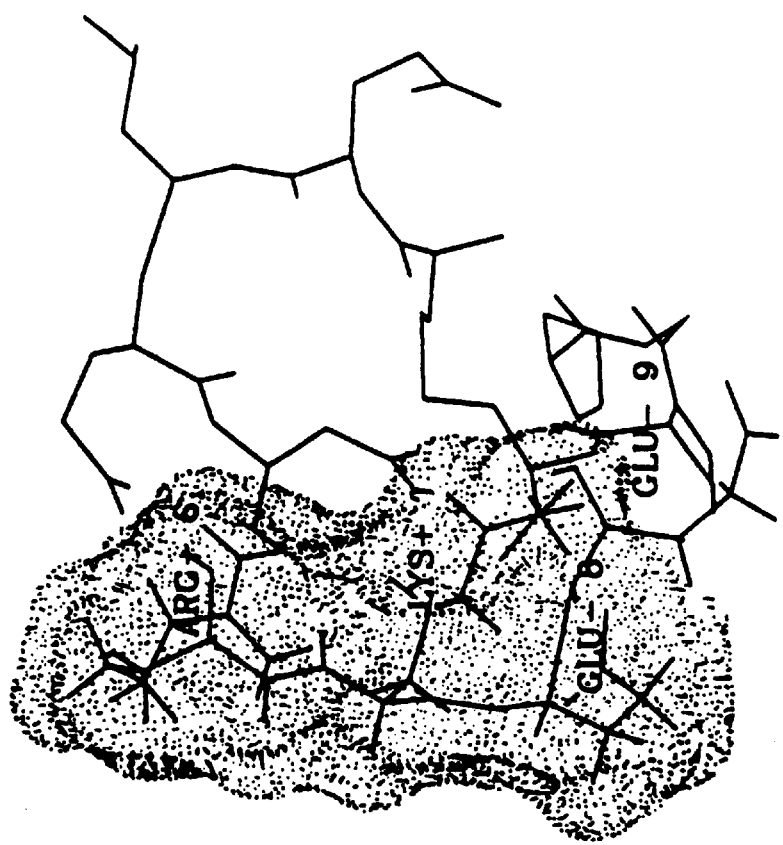

The solution structure of PEPTIDE 1 was characterized by two-dimensional NMR and distance constrained molecular dynamics. Several long range i, i+3 NOE's were observed, however, no i, i+4 NOE's were recorded. The results of the distance constrained molecular dynamics is shown in FIG. 9A. This conformer of protide is representative of a family of convergent structures that were obtained, which have a root mean square (RMS) variation in backbone position of ~0.5Å.

A detailed comparison of the proposed structure of protide with that of residues 86–96 of L3T4 showed that the peptide region from Arg(6) to Glu(9), which contains a putative binding surface, forms an exposed surface in the proposed conformation similar to that presented in the native protein. Other regions of PEPTIDE 1 (SEQ ID 1), however, showed little or no similarity to the L3T4 protein.

The steric constraints imposed by cyclization and the PGP "bend" sequence seems to sufficiently fix the secondary structures of the family of conformers, such that the appropriate contact face is exposed. The backbone and especially the side chains of the amino acids in the surface exposed region are flexible and have an appropriate electrostatic surface that may be energetically accessible even though the proposed backbone structure of protide differs from the L3T4 domain.

Example 4
Circular Dichroism Measurement

All of the CD measurements were performed on a Jobin Yvon (Edison, N.J.) CD6 spectrophotometer using circular quartz cells with a path length of 0.05 cm. The concentration of the peptide was 0.2 mg/ml in 10 mM potassium phosphate. Each measurement was the average of four repeated scans in steps of 0.2 nm, with an integration time of 2 seconds. The CD curves were analyzed using the CCA/Licomb and Provencher Least Squares programs.

In aqueous solution, CD spectra of PEPTIDE 1 (SEQ ID NO:1) show a strong negative band at or below 200 nm. This type of spectra often reflects a lack of periodic secondary structure. Addition of 30% trifluoroethanol or reduction of the disulfide bond with dithiothreitol did not appreciably alter the CD spectra.

Example 5
Cell Lines

22D11 is a CD4+, PCC specific T cell hybridoma, maintained in DMEM supplemented with 1 mM sodium pyruvate, 1 mM L-glutamine, 50 mM MEM nonessential amino acids, 50 mM MEM essential amino acids, penicillin (100 U/ml), streptomycin (100 μg/ml), and 10% heat-inactivated FCS, obtained from Yvonne Patterson, University of Pennsylvania, Philadelphia, Pa. D10.G4.1 is a CD4+ conalbumin-specific T cell clone and was obtained from ATCC, Rockville, Md. (ATCC #TIB224). Clones were stimulated every 10 to 14 days with 100 μg/ml Ag and feeder cells (C3H irradiated spleen cells) in RPMI 1640 supplemented with 1 mM glutamine, 5×10$^5$ M 2-ME, and penicillin-streptomycin. CT20 is an IL-2 dependent T cell clone, and was maintained in RPMI 1640, 10% FCS, and supplemented with Lymphocult (Biotest, Denville, N.J.), a source of IL-2. The hybridomas GK1.5 (αL3T4), 145-2C11 (αCD3ε), H57-597 (αTCR-βC) and MKD6 (αI-A$^d$) were maintained as described for example, by Wilde et al., *J. Immunol.* 1983, 131, 2178; Leo et al., *Proc. Natl. Acad. Sci. U.S.A.* 1987, 84, 1374; Kubo et al., *J. Immunol.* 1989, 142, 2736; and Kappler et al., *J. Exp. Med.* 1981, 53, 1198.

Example 6
Mixed Lymphocyte Reaction

The mixed lymphocyte reaction (MLR) is the response of one individual's T lymphocytes to those of a major histocompatibility complex (MHC) mismatched donor. CD4+ T cells recognize the foreign MHC proteins and proliferate in response to this, in a manner highly dependent on the CD4 molecule.

Mice were sacrificed and spleens aseptically removed. Cell suspensions were made by gently pressing spleens through nylon mesh, washing cells with RPMI 1640 and hypotonic lysis of red blood cells. After 3 washes in RPMI 1640, cells were resuspended in complete medium (RPMI 1640, 10% heat inactivated FCS, 2 mM L-glutamine, penicillin/streptomycin, and 5×10$^5$2-ME). 1×10$^5$ responder cells (BALB/c spleen cells) were incubated with 1×10$^5$ stimulator cells (C3H spleen cells, 2000 rad irradiated) in triplicate in round bottom 96 well plates (final volume 200 $\mu$l), and incubated with the indicated concentration of peptide (0.01, 0.1, 1, 10, 100 and 1000 $\mu$M peptide) for 5 days at 37° C., 5% CO$_2$. 1 $\mu$Ci/WELL OF [$^3$H] TdR was added 12 hours before thymidine incorporation was measured. Labelled DNA from cells was harvested onto glass fiber filters with a PHD cell harvester (Cambridge, Mass.), and CPM determined by liquid scintillation counting with the use of a 1209 Rackbeta (LKB, Piscataway, N.J.).

Example 7

Figure 2:
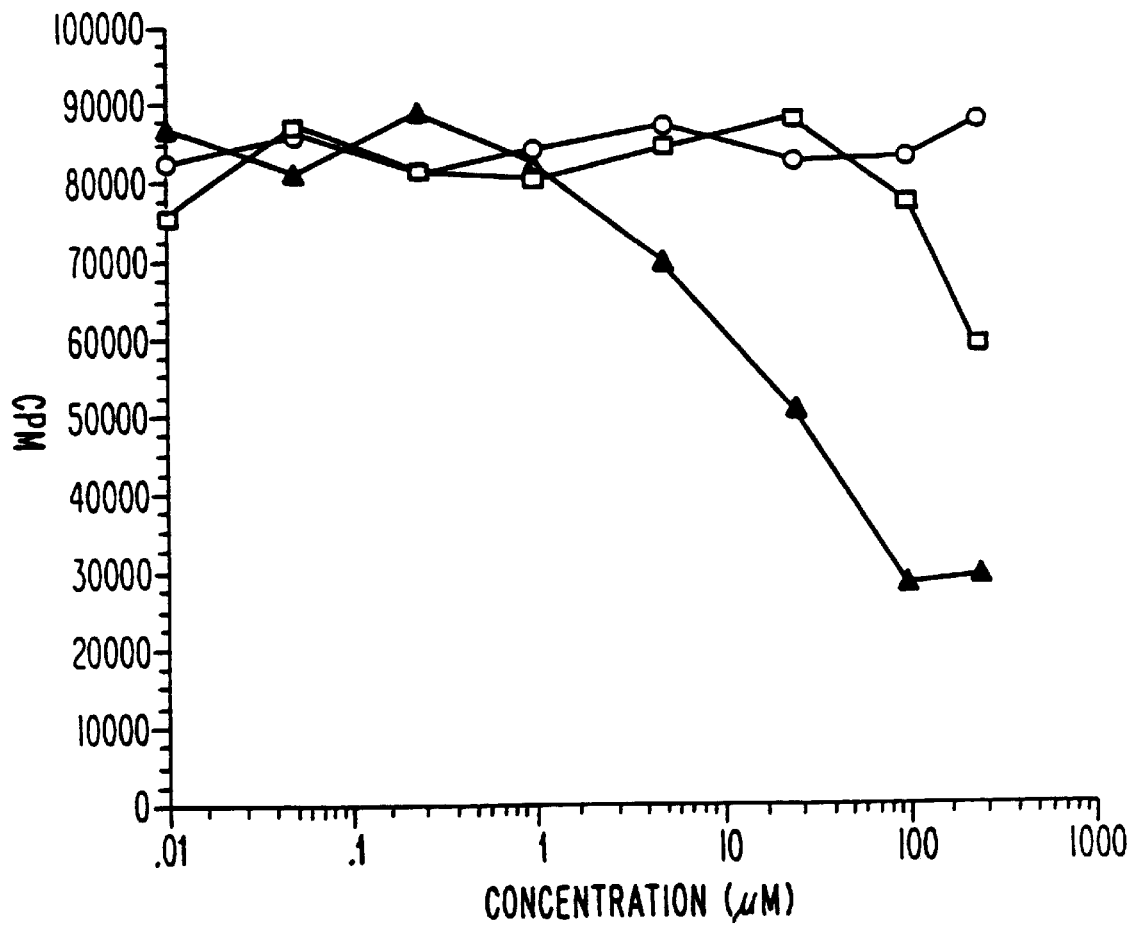
FIG. 2 is a graph illustrating the effects of SEQ ID NO:1 (murine CDR3 analog represented by (▲)) and control peptides SEQ ID NO:9 (mCDR3 scramble represented by (○)) and SEQ ID NO:3 (human CDR3 analog represented by (□)) on a BALB/c anti-C3H mixed lymphocyte reaction.

A MLR was performed as described in Example 6. Cells were incubated with a 0.01, 0.1, 1, 10, 100, and 1000 $\mu$M of each of the following peptides: SEQ ID NO:1 (mPGPtide), and control peptides, SEQ ID NO:3 (hPGPtides) and SEQ ID NO:13 (mCDR3 scramble). SEQ ID NO:1 exhibited inhibitory activity at low concentrations of peptide, while control peptides SEQ ID NO:3 and SEQ ID NO:13 exhibited little or no activity. FIG. 2 demonstrates the immunosuppressive effect of SEQ ID NO:1-(mPGPtide) on a CD4 dependent mixed lymphocyte reaction (MLR), in a BALB/c (H-2D) anti C3H (H-2K) alloresponse. Activity was approximately 85000 CPM after the addition of 0.01 $\mu$M SEQ ID NO:1, and approximately 30000 CPM after the addition of 200 $\mu$M SEQ ID NO:1. SEQ ID NO:3 demonstrates that the possession of the PGP motif is not, in itself, sufficient for biological activity. Activity was approximately 75000 CPM at 0.01 $\mu$M SEQ ID NO:3, and approximately 60000 CPM after the addition of 200 $\mu$M SEQ ID NO:3. Similarly, activity was approximately 80000 CPM after the addition of 0.01 $\mu$M of SEQ ID NO:13, and approximately 90000 CPM after the addition of 200 $\mu$M SEQ ID NO:13.

As in previous studies with L3T4 CDR3 analogs, McDonnell et al., *J. Immunol.* 1992, 149, 1626, the activity of SEQ ID NO:1 mapped directly to the T cell, as pretreatment of the responding T cells and not the antigen presenting cells inhibited stimulation. Moreover, the immunosuppressive effects of SEQ ID NO:1 were specific for signals generated through the T cell receptor complex, as no inhibition of T cell responses to IL-2 or LPS mediated B cell stimulation was seen. These data suggests that the mechanism of action of SEQ ID NO:1 is the disruption of a cis-type CD4 interaction, uncoupling it from the normal T cell activation cascade.

Example 8

Figure 3:
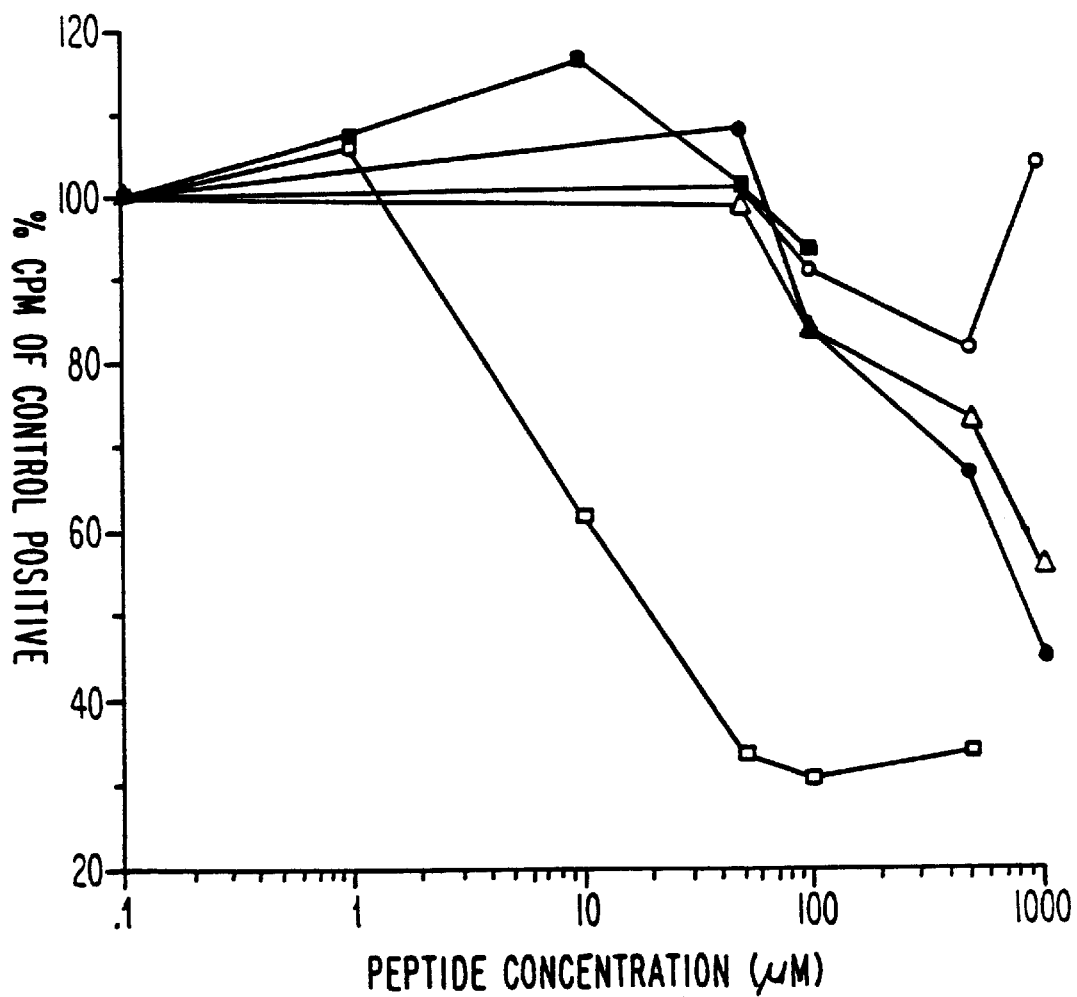
FIG. 3 is a graph illustrating the effects of SEQ ID NO:2 (h84-101 C—C), sCD4 (a soluble recombinant form of the two amino terminal domains of the CD4 protein), SEQ ID NO:14 (h18-40 linear), and control peptides SEQ ID NO:13 (h84-101 scramble) and SEQ ID NO:12 (h84-101 linear) on a human mixed lymphocyte reaction.

A MLR was performed as described in Example 6 using 0.1, 1, 10, 100, 500 and 1000 $\mu$M of peptides sCD4, SEQ ID NO:2, SEQ ID NO:12, SEQ ID NO:13 and SEQ ID NO:14. SEQ ID NO:2 (h84-101 C—C) exhibited inhibitory activity at low concentrations as compared to sCD4, SEQ ID NO:14 (h18-40 linear), SEQ ID NO:13 (h84-101 scramble) and SEQ ID NO:12 (h84-101 linear) which exhibited little or no activity, even at higher concentrations of peptide. FIG. 3 illustrates the data which demonstrates the ability of the human CD4 CDR3 analog SEQ ID NO:2 (h84-101 C—C) to inhibit the proliferative response of the MLR; half maximal inhibition is seen at low micromolar concentrations (approximately 30% CPM of the positive control at 500 $\mu$M peptide). sCD4 and SEQ ID NO:14 (CD4 18-40) showed some inhibition (between about 45% and 55% CPM of the positive control at 1000 $\mu$M peptide), while SEQ ID NO:12 (h84-101 linear) and SEQ ID NO:13 (h84-101 scramble) showed little or no inhibition. SEQ ID NO:12 (h84-101 linear) exhibited about 95% CPM of the positive control at 100 $\mu$M peptide, while SEQ ID NO:13 (h84-101 scrambled) exhibited about 100% of the positive control at 500 $\mu$M peptide.

Example 9

Figure 4:
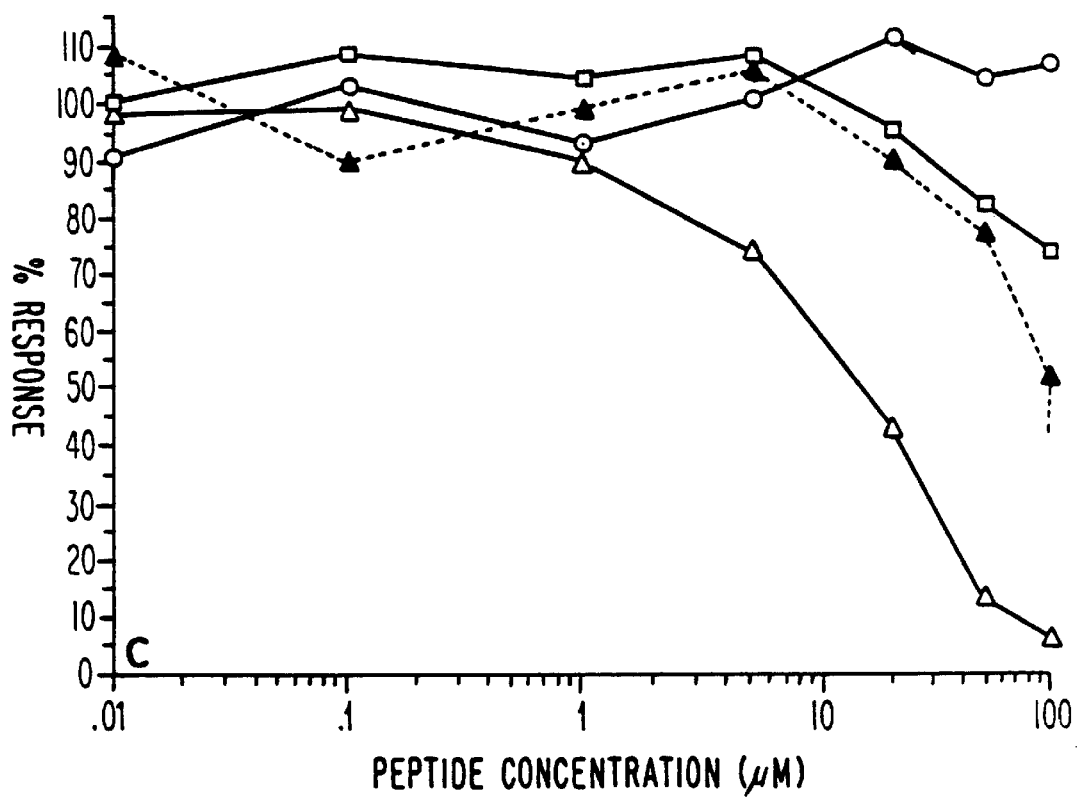
FIG. 4 is a graph illustrating the effects of SEQ ID NO:7 (m86-104 C—C, (Δ)), SEQ ID NO:8 (m86-104 linear, (□)), SEQ ID NO:9 (m86-104 scramble, (○)), and SEQ ID NO:10 (m86-103 C—C, (▲)) on a BALB/c anti-C3H mixed lymphocyte reaction. SEQ ID NO:7 exhibited inhibitory activity at low concentrations of peptide. SEQ ID NO:8 and SEQ ID NO:10 showed limited activity at higher concentrations of peptide and SEQ ID NO:9 was inactive.

A MLR was performed as described in Example 6 using 0.01, 0.1, 1, 5, 20, 50 and 100 $\mu$M of SEQ ID NO:7, SEQ ID NO:8, SEQ ID NO:9 and SEQ ID NO:10. Murine peptides SEQ ID NO:7 (m86-104 C—C), SEQ ID NO:8 (m86-104 linear), SEQ ID NO:9 (m86-104 scramble), and SEQ ID NO:10 (m86-103 C—C) were tested for their effects on MLR in a BALB/c (H-2D) anti-C3H (H-2K) alloresponse. SEQ ID NO:7 exhibited inhibitory activity at low concentrations of peptide. SEQ ID NO:8 and SEQ ID NO:10 showed limited activity at higher concentrations of peptide and SEQ ID NO:9 was inactive. FIG. 4 illustrates the ability of the CDR3 analogs to inhibit L3T4-dependent responses. SEQ ID NO:7 exhibited suppressive activity at the low micromolar range. At 20 $\mu$M, SEQ ID NO:7 exhibited approximately 45% CPM of a positive control, and at 100 $\mu$M exhibited approximately 0% CPM of a positive control. Both peptides with intact sequence but conformational alteration (SEQ ID NO:8 and SEQ ID NO:10) show very limited activity and only at the highest concentrations tested. At 20 $\mu$M, SEQ ID NO:8 and SEQ ID NO:10 exhibited from about 95% to about 100% CPM of a control. At 100 $\mu$M, SEQ ID NO:8 exhibited about 80% CPM of a control and 10 exhibited about 55% CPM of a control. SEQ ID NO:9 showed little or no activity, exhibiting approximately 100% CPM of a control regardless of the concentration of peptide added. The inactivity of the scramble peptide indicates that the negative charge is not sufficient to suppress immunological responses. Thus, presentation of this charge in the context of both sequence as well as conformation is necessary for biological activity. MLR generated against B and D allotypes were also performed and identical inhibition was seen, indicating that inhibition is not limited to H-2K restricted responses.

Example 10

A MLR was performed as described in Example 6. h84-101 C—C, SEQ ID NO:4, SEQ ID NO:5, SEQ ID NO:6, SEQ ID NO:11, (SEQ ID NO:4+SEQ ID NO:5), and a monoclonal antibody directed against CD4 (OKT4A) were tested for their effect on MLR in a BALB/c (H-2D) anti C3H (H-2K) alloresponse. MLR was also performed without the addition of peptide or antibody (MLR). Each peptide individually has inhibitory activity to a moderate level (30–50%), but when two analogs are added together (SEQ ID NO:4 and SEQ ID NO:5) the effect was synergistic and the inhibition approached 100%, as compared to a monoclonal antibody directed against CD4 (OKT4A). The results are summarized in Table II.

TABLE II

| PEPTIDE or ANTIBODY | CPM |
| --- | --- |
| MLR (No peptide or antibody) | 66000 |
| control peptide | 62500 |
| SEQ ID NO:2 | 20000 |
| SEQ ID NO:5 | 48000 |
| SEQ ID NO:4 | 42000 |
| SEQ ID NO:6 | 50000 |
| SEQ ID NO:4 + SEQ ID NO:5 | 18000 |
| OKT4A | 12000 |

Example 11
Inhibition of IL-2 production

IL-2 production was assayed by culturing $1\times10^5$ T cell hybridoma-22D11 cells with $5\times10^5$ feeder cells (irradiated C3H spleen cells) and 100 μg/ml PCC, or $1\times10^5$ 22D11 in H57-597-(αTCR) coated wells, and the indicated concentration of peptide (0.01, 0.1, 1, 10, 50 and 100 μM) in triplicate in round-bottom 96-well plates. At 24 hours cells were pelleted and supernatants transferred to another 96-well plate with $1\times10^4$ CT20 cells/well. Cells were incubated with 1 μCi [$^3$H]TDR well for the final 4 hours of a 24 hour incubation. Labeled DNA from cells was harvested onto glass fiber filters with a PHD cell harvester (Cambridge, Mass.), and CPM determined by liquid scintillation counting with the use of a 1209 Rackbeta (LKB, Piscataway, N.J.). Responses were I-$E^k$ restricted, PCC specific.

Example 12

Figure 5:
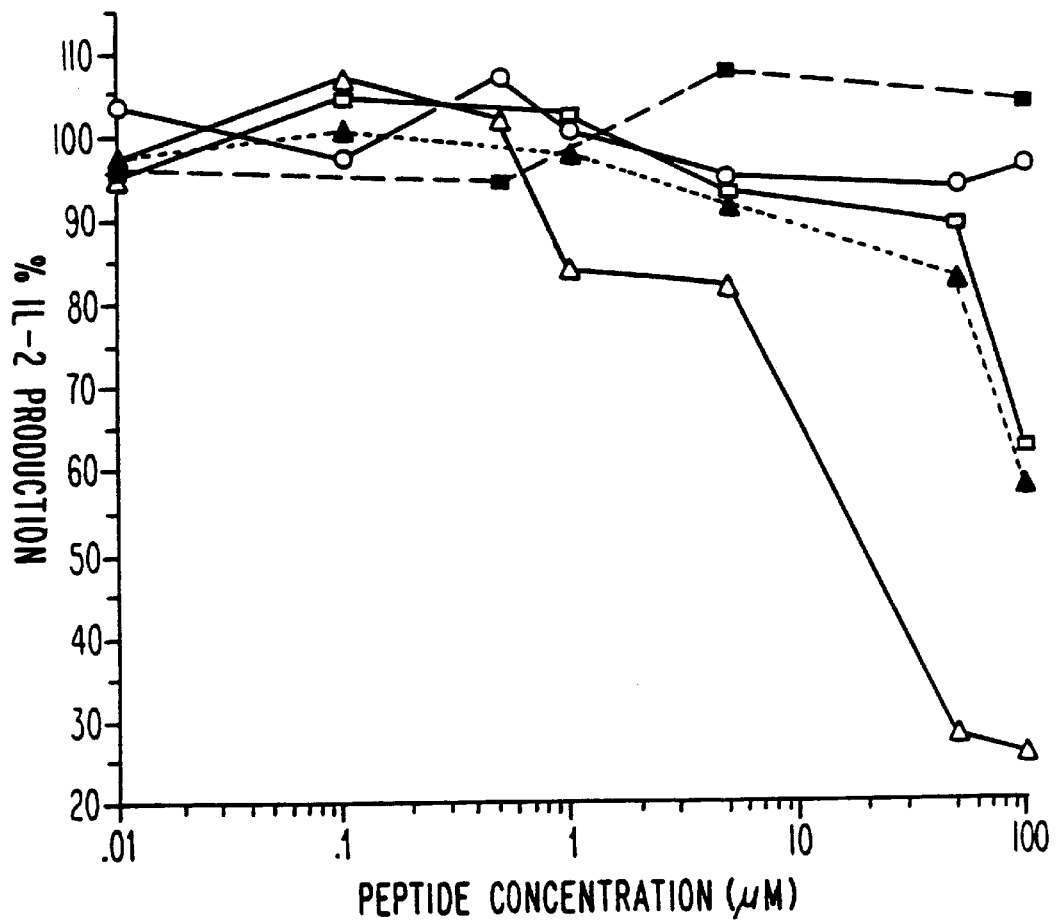
FIG. 5 is a graph illustrating the effects of SEQ ID NO:7 (m86-104 C—C, (Δ)), SEQ ID NO:8 (m86-104 linear, (□)), SEQ ID NO:9 (m86-104 scramble, (○)), SEQ ID NO:10 (m86-103 C—C, (▲)), and SEQ ID NO:11 (unrelated control, (■)) on IL-2 production.

An assay was performed in accordance with Example 11 to determine the effect of SEQ ID NO:7, SEQ ID NO:8, SEQ ID NO:9, SEQ ID NO:10 and SEQ ID NO:11 on IL-2 production. SEQ ID NO:7 exhibited inhibitory activity at low concentrations of peptide. SEQ ID NO:8 and SEQ ID NO:10 showed limited activity at higher concentrations of peptide and SEQ ID NO:9 and SEQ ID NO:11 were inactive. FIG. 5 illustrates that SEQ ID NO:7 (m86-104 C—C) exhibited suppressive activity of IL-2 production at the low micromolar range. Administration of 50 μM SEQ ID NO:7 inhibited IL-2 production to about 30% of IL-2 production of a control, and administration of 100 μM SEQ ID NO:7 inhibited IL-2 production to about 25% IL-2 production of a control. Both peptides with intact sequence but conformational alteration (SEQ ID NO:8 (m86-104 linear) and SEQ ID NO:10 (m86-103 C—C)) showed limited activity and only at the highest concentrations tested. Administration of 50 and 100 μM SEQ ID NO:8 resulted in about 90% and 60% IL-2 production of a control, respectively. Similarly, administration of 50 and 100 μM SEQ ID NO:10 resulted in about 85% and 70% IL-2 production of a control, respectively. SEQ ID NO:9 (m86-104 scramble) exhibited little or no activity, exhibiting approximately 100% IL-2 production of a control.

Example 13
T Cell Proliferation Assay

For T cell proliferation assays D10.G4.1, cells were used 10 to 14 days post-stimulation, and viable cells were selected by centrifugation over Ficoll (Pharmacia Fine Chemicals, Piscataway, N.J.) and washed three times. The $1\times10^5$ D10 cells were cultured with $5\times10^5$ feeder cells, 100 μg/ml conalbumin, and the indicated peptide concentration (0.01, 0.1, 0.5, 1, 5, 25, 50, and 100 μM) in triplicate in round-bottom plates for 72 hours. Cells were incubated with 1 μCi/well of [$^3$H]TDR for the final 16 hours. Cells were harvested and incorporated radioactivity counted as above. Responses were I-$A^k$ restricted, conalbumin specific. SEQ ID NO:7 exhibited inhibitory activity at low concentrations of peptide. SEQ ID NO:8 and SEQ ID NO:10 showed limited activity at higher concentrations of peptide and SEQ ID NO:9 and SEQ ID NO:11 were inactive.

Figure 6:
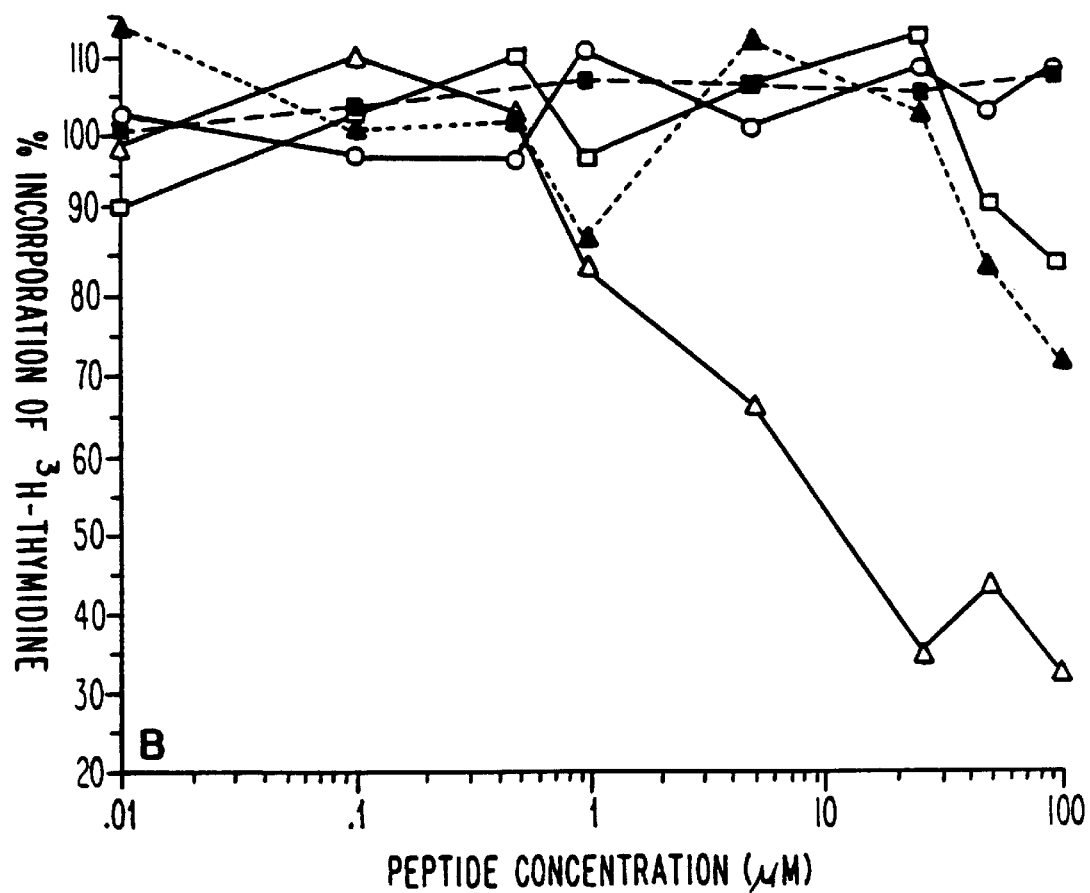
FIG. 6 is a graph illustrating the effects of SEQ ID NO:7 (m86-104 C—C, (Δ)), SEQ ID NO:8 (m86-104 linear, (□)), SEQ ID NO:9 (m86-104 scramble, (○)), SEQ ID NO:10 (m86-103 C—C, (Δ)), and SEQ ID NO:11 (unrelated control, (■)) on T cell proliferation.

FIG. 6 illustrates the data showing that SEQ ID NO:7 (m86-104 C—C) exhibited suppressive activity of T cell proliferation at the low micromolar range. At 5 μM, peptide concentration T cell proliferation was reduced to about 65% of control (SEQ ID NO:11). From 25 μM to 100 μM, peptide concentration T cell proliferation was reduced to about 30% of control. Both peptides with intact sequence but conformational alteration (SEQ ID NO:8 (m86-104 linear) and SEQ ID NO:10 (m86-103 C—C)) show very limited activity and only at the highest concentrations tested. SEQ ID NO:8 exhibited about 80% T cell proliferation of control at 100 μM peptide concentration, and SEQ ID NO:10 exhibited about 75% T cell proliferation of control at 100 μM peptide concentration. SEQ ID NO:9 (m86-104 scramble) was completely inactive exhibiting 100% T cell proliferation of control at 100 μM peptide concentration.

Example 14
Phytohemagglutinin T Cell Proliferation Assay

Figure 7:
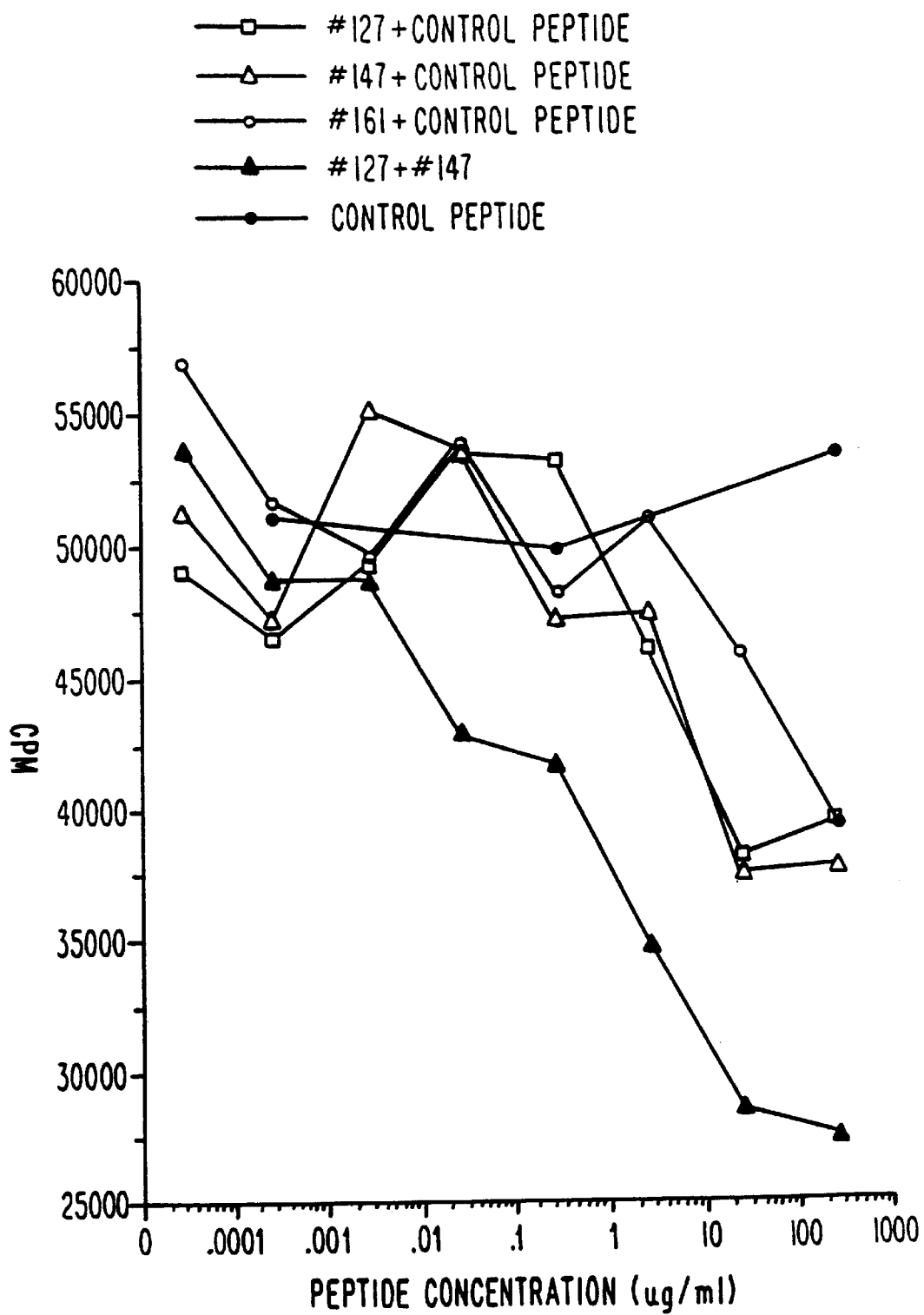
FIG. 7 is a graph illustrating the effects of SEQ ID NO:4+control peptide (Δ), SEQ ID NO:5+control peptide (□), and SEQ ID NO:6+control peptide (○), SEQ ID NO:4+ SEQ ID NO:5 (▲) and control peptide (●) on the inhibitory effect of PHA mediated stimulation of T cells.

The mitogen phytohemagglutinin (PHA) activates T cells by cross-linking CD3/TCR complexes. Human blood is collected from volunteer donors. Lymphocytes are purified by separation over a Ficoll gradient. T cells are separated by rosetting to sheep red blood cells. The enriched T cell population is stimulated with 5 μg/ml phytohemagglutinin (PHA). FIG. 7 illustrates the ability of the D2 peptide analogs to inhibit T cell proliferation in response to PHA stimulation. 0.000025, 0.00025, 0.0025, 0.025, 0.25, 2.5, 25, and 250 μM peptide concentrations were tested. As in the MLR assays, each D2-derived peptide showed a moderate dose-dependent inhibitory activity alone. Results are illustrated in FIG. 7. Addition of 0.25 μM SEQ ID NO:4, SEQ ID NO:5, SEQ ID NO:6, and SEQ ID NO:11 resulted in 47000 CPM, 53500 CPM, 48000 CPM, and 50000 CPM, respectively. When SEQ ID NO:4 and SEQ ID NO:5 were added together M the percentage inhibition seen was significantly increased. 0.25 μg (total) of SEQ ID NO:4 and SEQ ID NO:5 added together resulted in 41500 CPM. The amount of peptide needed for inhibition was reduced two orders of magnitude, indicating a synergistic effect between the two peptides. For example, only 2.5 μg (total) of SEQ ID NO:4 and SEQ ID NO:5, combined, resulted in 34500 CPM. 250 μg SEQ ID NO:4, SEQ ID NO:5 and SEQ ID NO:6 resulted in 38000, 39500, and 39500 CPM respectively.

Example 15
Cell Death Assay

For cell death assay flat-bottomed 96-well culture plates were coated with 100 μl of mAb at 100 μg/ml for 4 hours at 37° C.; then the plates were incubated with indicated concentration of peptide or antibody. Peptides were used at 100 μM. Monoclonal antibodies GK1.5 (α-L3T4), 145-2C11 (α-CD3), and the negative control MKD6 (α-I $A^d$) were used at saturating concentrations. At 24 hours, 100 μl of culture supernatant were removed and assayed for IL-2 production as described above. Thereafter, cells were harvested and cell viability was monitored by inhibition of [$^3$H]TdR uptake and by the trypan blue exclusion test. The results are expressed as the mean of triplicate cultures.

SEQ ID NO:7 (m86-104 C—C) inhibited receptor-mediated cell death by the anti-TCR-stimulated 22D11 cells.

Both peptides with intact sequence but conformational alteration SEQ ID NO:8 (m86-104 linear) and SEQ ID NO:10 (m86-103 C—C) showed very limited activity and only at the highest concentrations tested. SEQ ID NO:9 (m86-104 scramble) was completely inactive. Results are summarized in Table III.

TABLE III

| H57-587 coated plates | Reagents added | IL-2 secreted (U/ml) | % [$^3$H]Tdr uptake | % viability (trypan blue) |
|---|---|---|---|---|
| − | none | 0 | 100 (1.21 × 10$^5$) | 98 |
| + | none | 148 | 8 | 21 |
| + | GK1.5 | 27 | 77 | 75 |
| + | 145-2C11 | 15 | 91 | 87 |
| + | MKD6 | 150 | 10 | 24 |
| + | SEQ ID NO:7 | 33 | 69 | 74 |
| + | SEQ ID NO:8 | 119 | 21 | 37 |
| + | SEQ ID NO:9 | 145 | 7 | 22 |

Example 16

Effect of peptide on BALB/c spleen cell proliferative response to anti-CD3, LPS, and rIL-2

Figure 8:
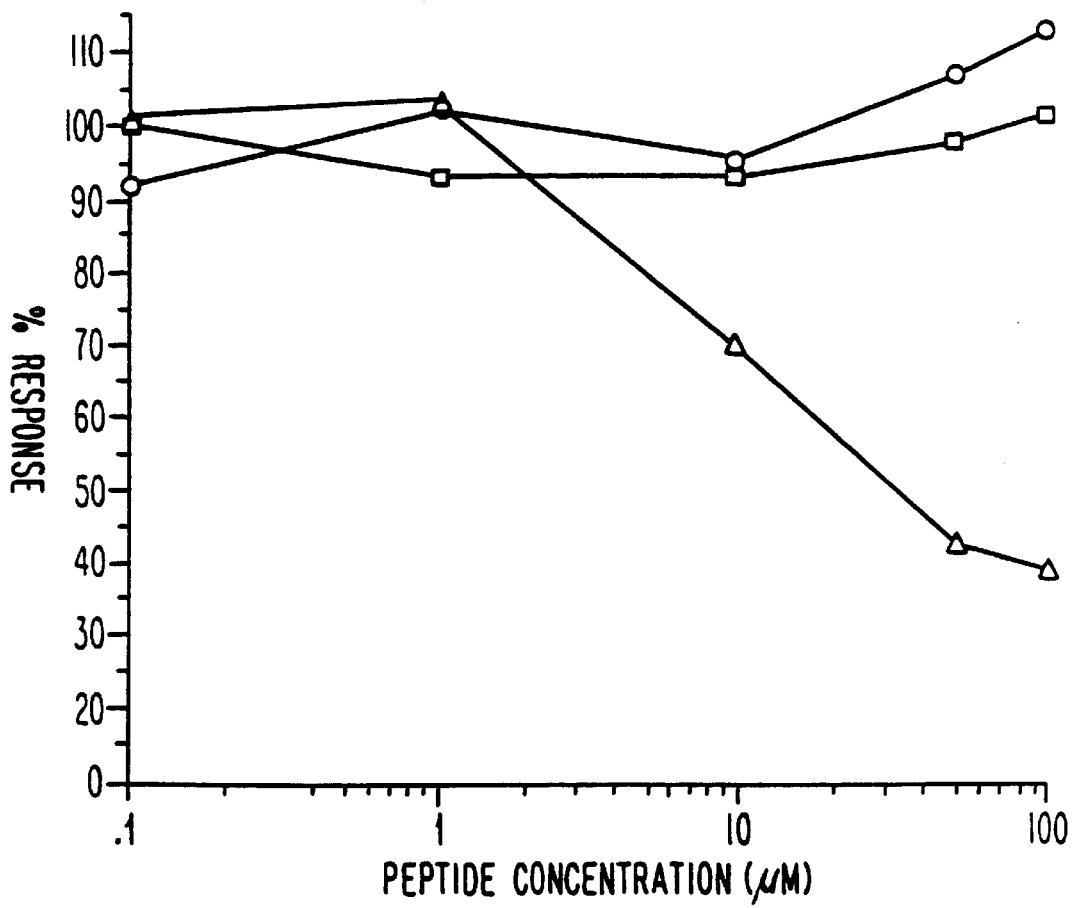
FIG. 8 is a graph illustrating the effects of SEQ ID NO:7 (m86-104 C—C) on the proliferative effects of αCD3 (145-2C11, (Δ)), LPS (□), and rIL-2 (○).

The effect of SEQ ID NO:7 (m86-104 C—C) on the proliferative effect of anti-CD3 (145-2C11), LPS, and rIL-2 was tested. BALB/c spleen cells are plated at 1×10$^5$ spleen cells/well in round-bottom 96-well plates and stimulated with either anti-CD3 (145-2C11, 1% tissue culture supernatants), lipopolysaccharide (LPS, 10 μg/ml), or mouse rIL-1 (100 U/ml). SEQ ID NO:7 inhibited the proliferative response of T cells to αCD3 but had little or no effect on the proliferative response of T cells to LPS or rIL-2. As can be seen in FIG. 8, the peptide showed no inhibition of LPS-mediated B-cell proliferation, thus demonstrating the specificity of inhibitory activity. The proliferative response of cells to αCD3 was depressed in a dose dependent manner while no effect was seen on the proliferative response of cells to rIL-2, indicating that the ability to inhibit T cell activation appears to be limited to signals generated through the TCR.

Example 17

The in vitro activity of the murine 86-103 peptide (containing an introduced non-CD4 cysteine at position 103 in order to create a circular, covalently closed analog) resides within only a small portion of the peptide, residues Arg-91, Lys-92, Glu-93 and Glu-94. Furthermore, the activity of these amino acids critically depends on their spacial juxtaposition. Thus, contrary to the expectation that the backbone folding and sequence are critical to the potential activity of the CDR3-like analogs, it is the correct positioning of the amino acid side chain atoms in space to create a "surface" that confers the complete activity of the analogs.

The activity of newly developed CD4-derived analogs can be shown to provide utility in the treatment of autoimmune diseases such as Multiple Sclerosis. Multiple sclerosis is an autoimmune disease with unknown etiology. It involves a chronic relapsing inflammatory response that results in demyelination in the central nervous system (CNS). Although the mechanism of destruction of neuronal myelin sheaths in the effector phases of the disease are unclear and may be due to non-specific cellular or cytokine activity, the majority of the small lymphocytes found in early lesions are of the CD4+ helper/inducer T cell subset (Raine and Scheinberg, (1988) *J Neuroimmunol.* 120:189–201). The level of CD4+ T cell infiltration into the CNS is thought to correlate with multiple sclerosis attacks, despite controversy over what antigens (such as myelin basic protein or proteolipids) might be stimulating the responses. Both the clinical course and clinical manifestations of multiple sclerosis are variable, depending upon the site of the CNS lesions, as well as the kinetics and progression of the disease.

Experimental allergic encephalomyelitis (EAE) is considered to be the best experimental animal model for the study of multiple sclerosis since it shares many of the same clinical and histopathological features as the human disorder. EAE can be elicited in several animal species, including mice, by inoculation of crude CNS tissue extracts, purified MBP, proteolipids, or synthetic polypeptides composed of the active portions of these antigenic molecules. Antigen is administered subcutaneously in conjunction with complete Freund's adjuvant (CFA) and, in our modification of the standard procedure, is given twice on days 0 and 7 for induction (Korngold et al., (1986) *Immunogenetics* 24:309–315, which is incorporated herein by reference). Symptoms of disease usually occur between 15–19 days after initial immunization and may last for up to 25 days. Mice usually recover from the acute EAE attack, but may relapse at a later time, or are susceptible to an enhanced disease episode upon further immunization. Clinical neurological symptoms in the mice are scored based on the extent of limb weakness and paralysis, and histopathological analysis reveals the extent of cellular infiltration into the CNS and demyelination. It is clear from the murine EAE model that CD4+ T cells are critical for induction of disease and a major goal of immunological research in the EAE and multiple sclerosis field has been to find an approach that can specifically inhibit those CD4+ T cells that are reacting to CNS antigens without compromising the entire immune system.

D-amino acid analogs of the CDR3-like domain of the CD4 protein were demonstrated to possess potent and useful therapeutic activities in treating autoimmune disorders, especially with regard to demyelinating diseases such as Multiple Sclerosis.

The following peptide, which is the reverse sequence of SEQ ID NO:1, was synthesized with using D-amino acids according to standard procedures and tested in relevant assays.

D amino acid CDR3-like peptide #1:
CPGPEEKRNELEC.

The all L-amino acid analog SEQ ID NO:1 was tested in the murine experimental allergic encephalomyelitis model for human Multiple Sclerosis. This analog was found to have no statistically significant effect on the course of disease progression.

The all D-amino acid peptide described above was shown to have dramatically intervened in the progression of this autoimmune disorder. The in vivo efficacy of the all D-amino acid reverse sequence analog demonstrates the therapeutic value of this compound.

Example 18

Effect of a CD4-CDR3-Like Analog on Clinical Incidence of EAE

SJL mice, which are highly susceptible to the induction of acute EAE, were immunized as described in Korngold et al., (1986) *Immunogenetics* 24:309–315. Accordingly, 1 mg of crude SJL mouse spinal cord homogenate (MSCH) was diluted in 0.15 ml phosphate buffered solution and emulsified in an equal volume of CFA. 0.15 ml of the inoculum was injected subcutaneously in each of two sites on the posterior flank of mice anesthetized with metaphane. A secondary inoculation, similar to the primary, was administered at 7 days. Mice were evaluated daily for symptoms of disease and graded 0–5: 0=no clinical expression of disease; 1=flaccid tail with or without mild hind leg weakness; 2=flaccid tail with moderate hind leg weakness; 3=severe hind leg weakness and mild forelimb weakness; 4=total hind leg paralysis associated with moderate forelimb weakness; and 5=quadriplegia or a moribund state.

Figure 10:
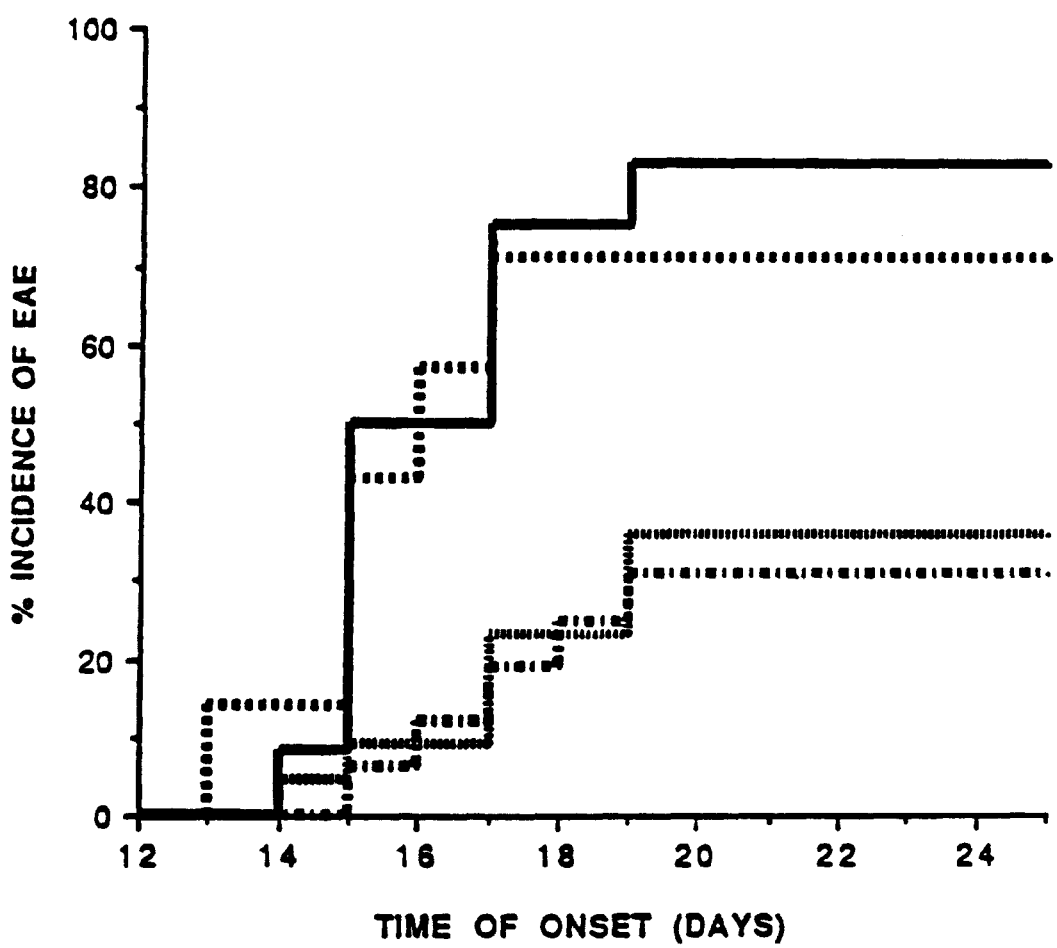
FIG. 10 is a graph which illustrates the level of incidence of EAE in untreated mice and those administered control peptide or D amino acid CDR3-like peptide #1.

The mice were divided into four groups: the first left untreated; the second injected on days 2 and 8 intravenously (i.v.) with 0.5 mg of the D amino acid CDR3-like peptide #1; the third injected on day 12 i.v. with the D amino acid CDR3-like peptide #1; and the fourth injected i.v. on days 2 and 8 with a control D-polypeptide of similar length to the D amino acid CDR3-like peptide #1. As demonstrated in FIG. 10, the level of incidence of EAE (mice with symptoms at any grade) in the untreated group reached 83% by day 19 of the experiment and a similar level was reached by the group treated with control peptide (71%). On the other hand, both groups treated with the D amino acid CDR3-like peptide #1 on either days 2,8, or day 12 only reached a maximum EAE incidence of 36% and 31%, respectively. The average time of initial onset in those mice which developed a symptom of disease was also later in mice treated with the D amino acid CDR3-like peptide #1 (day 17.1 and 17.0 for those treated on days 2,8 or day 12, respectively in comparison to days 15.6 and 15.2 for the untreated and control peptide groups, respectively).

Figure 11:
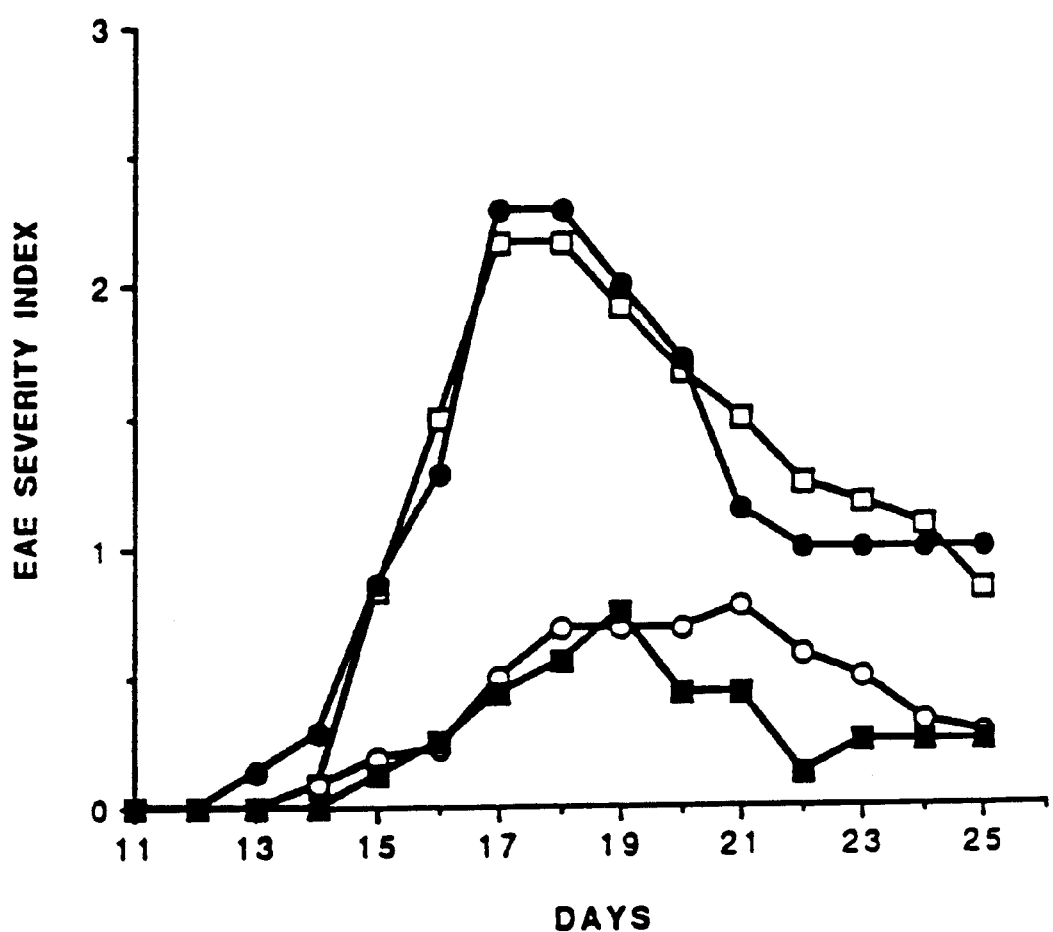
FIG. 11 is a graph which illustrates the severity grade in untreated mice and those administered control peptide those administered control peptide or D amino acid CDR3-like peptide #1.

Example 19
Effect of a D amino acid CDR3-like peptide #1 on Clinical Severity of EAE With the same experiment described above, mice from the different treatment groups were scored for the clinical expression of disease. As shown in FIG. 11, the mean EAE severity grade of mice in the untreated and control peptide groups reached a maximum of 2.17 and 2.29, respectively, between days 17–18 of the experiment, whereas the maximum severity levels reached with the groups given D amino acid CDR3-like peptide #1 on days 2,8, or day 12 were 0.77 and 0.75, espectively, with peak activity between days 19–21. The ifferences were statistically significant, by Tukey multiple analysis of variance, between: the untreated and the D amino acid CDR3-like peptide #1 day 2,8 treated group on days 16–19 and 24 (0.01:p<0.04); the untreated and the D amino acid CDR3-like peptide #1 day 12 treated group on days 16–24 (0.01≦p≦0.05); and the control peptide day 2,8 group and the D amino acid CDR3-like peptide #1 day 2,8 treated group on day 17 (p=0.02).

Figure 12:
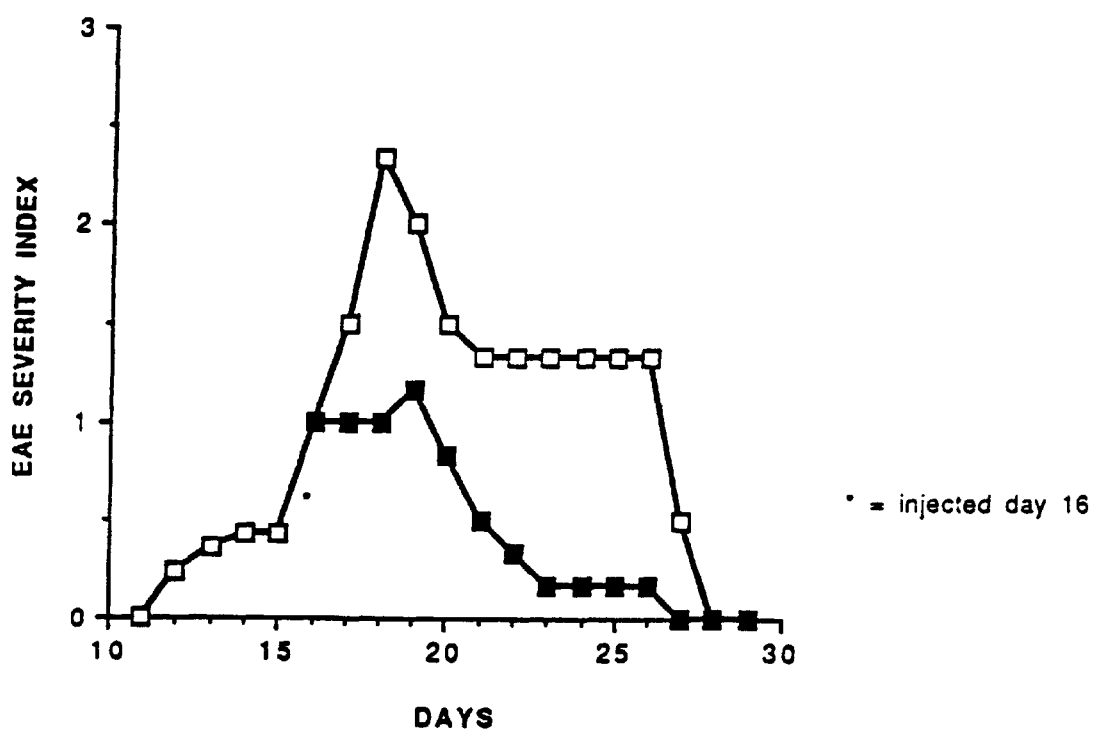
FIG. 12 is a graph which illustrates the severity grade in untreated mice and those administered control peptide those administered control peptide or D amino acid CDR3-like peptide #1 after onset of symptoms.

Example 20
Effect of D amino acid CDR3-like peptide #1 on Clinical Severity of EAE During the Effector Phase To investigate whether D amino acid CDR3-like peptide #1 could have an effect upon the development of EAE once symptoms have already appeared and therefore corresponding to the effector phase of the disease, 30 SJL mice were inoculated on days 0 and 7 with MSCH and CFA, as described above. 12 mice that had reached a grade 1 level of clinical EAE expression by day 16 were selected and randomly grouped to be left untreated or treated with 0.5 mg i.v. of D amino acid CDR3-like peptide #1. As demonstrated in FIG. 12, the untreated group of mice progressed in disease to an average of 2.4 by day 18, whereas those mice treated with D amino acid CDR3-like peptide #1 reached only a grade 1.17 of severity on day 19 and rapidly declined thereafter. At day 18, the difference between the untreated and treated groups was statistically significant (p=0.003).

Example 21
Phenotype and Functionality of T cells From Mice Challenged for EAE and Treated with D amino acid CDR3-like poptide #1

Figure 13:
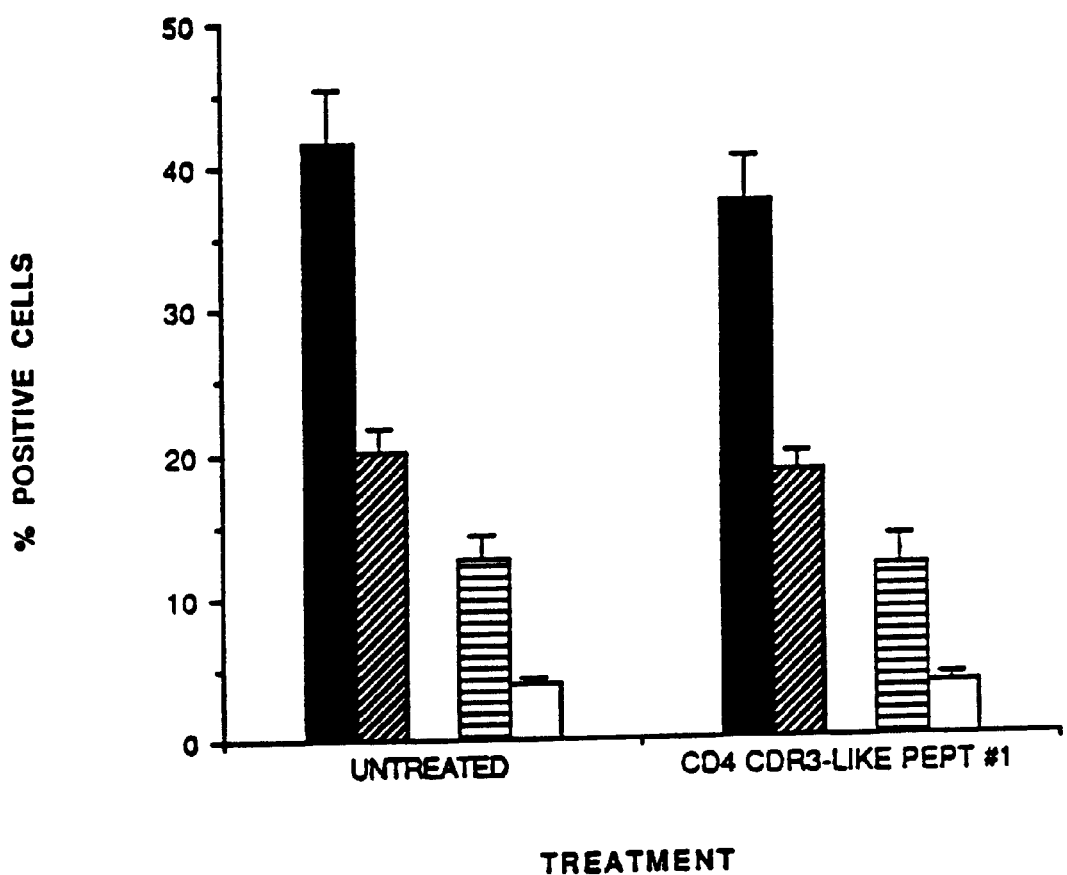
FIG. 13 is a bar graph which illustrates a comparison of the cellular compositions of the lymphoid organs in untreated mice and those administered D amino acid CDR3-like peptide #1.
Figure 14:
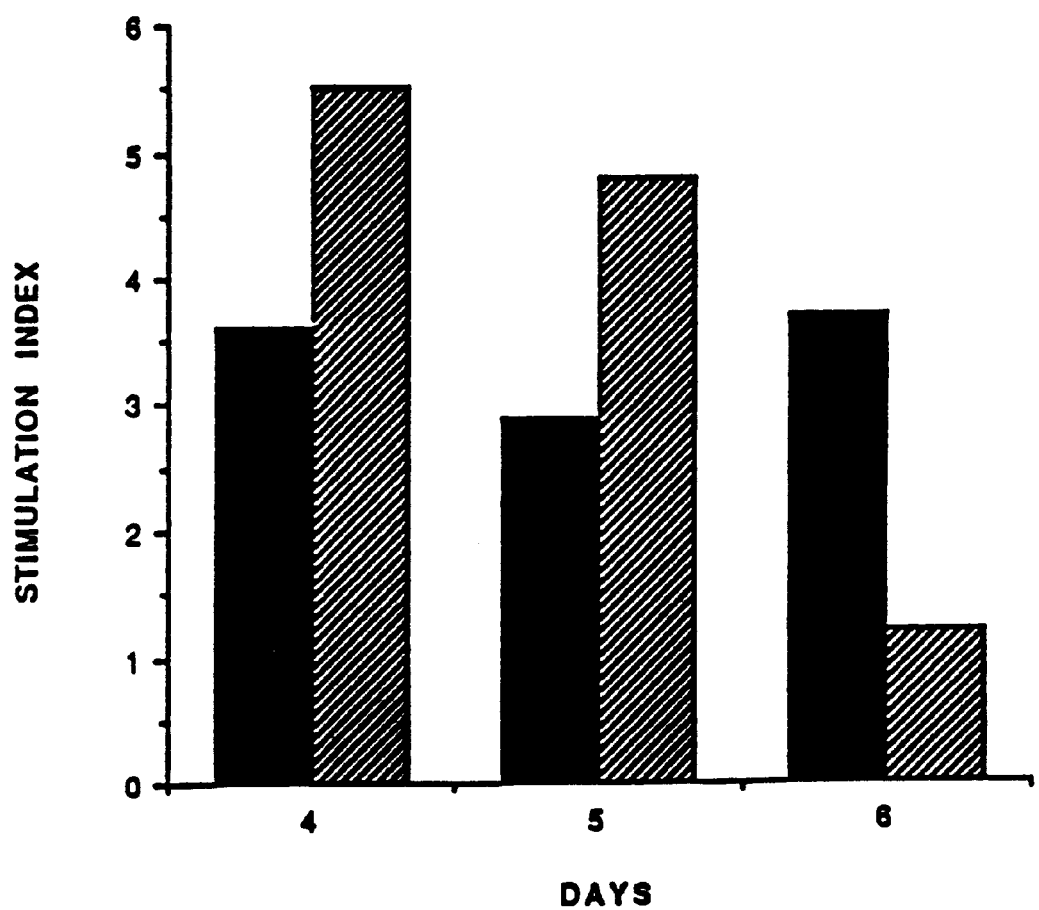
FIG. 14 is a bar graph which illustrates a comparison of the proliferative responses to the allogeneic MHC antigen (the stimulation index was calculated by dividing the allogeneic response, as measured by ³H-thymidine uptake, by the syngeneic response using irradiated SJL stimulator cells) by cells from untreated mice and those administered the D amino acid CDR3-like peptide #1.

SJL mice that had received the inoculation for EAE induction on days 0 and 7, and were either left untreated or treated with 0.5 mg iv D amino acid CDR3-like peptide #1 on day 12, were sampled on day 27 for the presence of CD4+ and CD8+ T cell subsets in the spleen and lymph nodes (pooled from cervical, axial, brachial, inguinal, and mesenteric nodes). Phenotypes of the cells was determined by flow cytometric analysis with FITC-labelled anti-murine CD4 and CD8 monoclonal antibodies. As shown in FIG. 13, the cellular compositions of the lymphoid organs in the two groups were equivalent. Of particular interest was the finding that there was no significant diminution of CD4+ cells in those mice treated with the D amino acid CDR3-like peptide #1 (0.76≦p≦0.99). In addition, lymph node cells from the D amino acid CDR3-like peptide #1 treated group were assayed for immune responsiveness in a mixed lymphocyte reaction to irradiated (1500 cGy) MHC-allogeneic stimulator spleen cells (CBA strain). As shown in FIG. 14, the D amino acid CDR3-like peptide #1 treated group gave equivalent, if not better, proliferative responses to the allogeneic MHC antigen (the stimulation index was calculated by dividing the allogeneic response, as measured by $^3$H-thymidine uptake, by the syngeneic response using irradiated SJL stimulator cells).

Example 22
The Effect of D amino acid CDR3-like peptide #1 on Development of GVHD Mediated by CD4+ T cells The following data support the use of CD4 analogs as therapeutics in individuals undergoing or recovering from transplantation procedures. Clinical bone marrow transplantation is an important therapeutic treatment for several diseases including high risk leukemia, aplastic anemia, and severe combined immunodeficiency. In addition, there is a wide range of metabolic and genetic disorders that can potentially be corrected by this approach. However, the usefulness of marrow transplantation is currently limited by several important risk factors, the principal one being graft-versus-host disease (GVHD), an often times lethal complication which occurs in a high proportion of transplants. The risk of GVHD can be reduced by HLA matching of the marrow donor and recipient, with a matched sibling being the primary choice. Yet, less than 30% of the patients in North America have an HLA-matched sibling, and therefore must seek suitable unrelated HLA-matched donors from the National Marrow Donor Program. The probability of finding an unrelated HLA-matched donor is currently on the order of 30–40% and will depend on the total number of donors registered. In both related and unrelated HLA-matched transplant situations, the risk of GVHD is still quite high due to disparity of non-HLA multiple minor histocompatibility (H) antigens. GVHD is somewhat higher in unrelated cases, as this increases the probability of differences at these loci.

It is clear that mature donor T cells contaminating the marrow inoculum are responsible for GVHD and several studies have shown that depletion of these T cells significantly diminishes the incidence of disease. However, the elimination of donor T cells has also resulted in a greater incidence of leukemic relapse. It seems important to provide at least some level of immunocompetency in these completely immunocompromised patients, to not only combat residual leukemia cells but also to counter opportunistic infections. In this respect, if a CD4-CDR3 analog can specifically diminish the subpopulation of donor CD4+ T cells that respond to minor H antigens of the host and are responsible for GVHD, the rest of immunity may be left intact to counteract leukemic relapse and infection.

Figure 15:
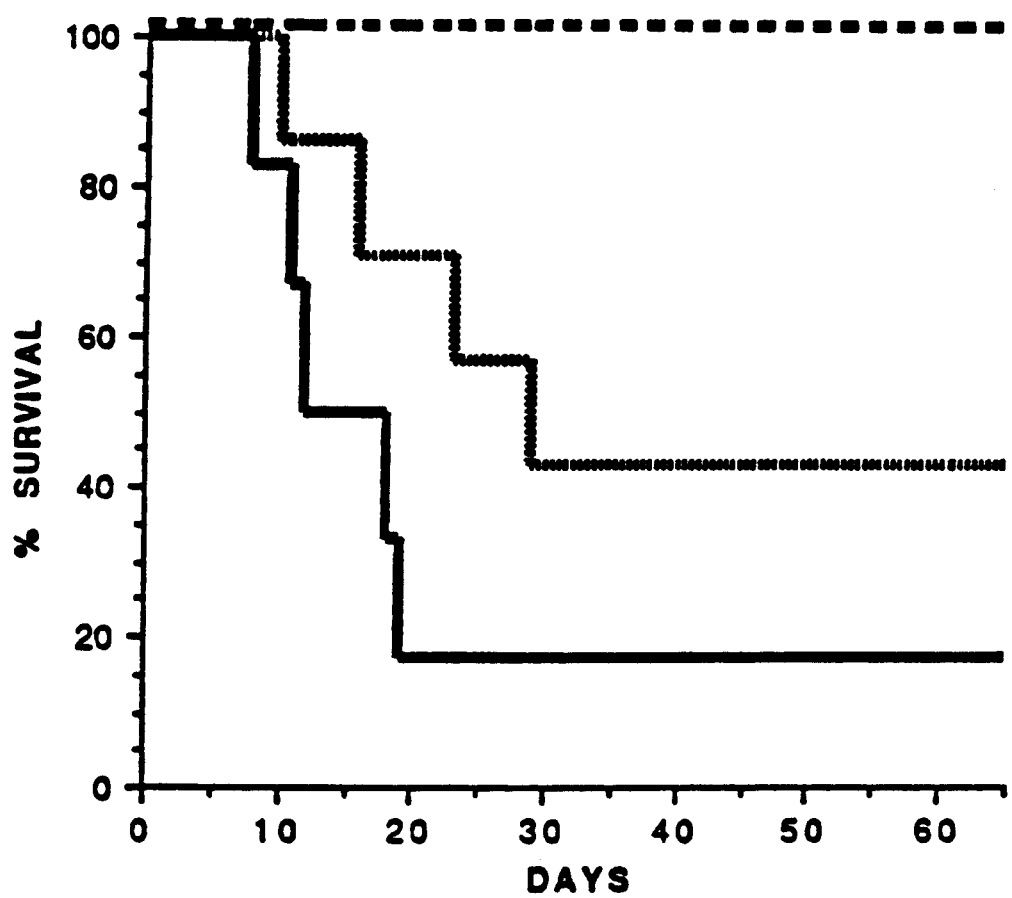
FIG. 15 is a graph illustrating the comparative survival rates of mice after the transplantation of 2×10⁶ B10.D2 CD4+ T cells when untreated and when treated with D amino acid CDR3-like peptide #1.

The transplantation of B10.D2 CD4+ T cells along with T-cell-depleted bone marrow has been shown previously to induce a lethal GVHD response in irradiated (850 cGy) DBA/2 mice (Korngold and Sprent, (1987) *J. Exp. Med.* 165:1552–1564). As shown in FIG. 15, the transplantation of 2×10⁶ B10.D2 CD4+ T cells resulted in an 83% incidence of lethal GVHD in DBA/2 recipients with a median survival time of 15 days. Transplantation of donor T-cell-depleted bone marrow alone resulted in complete survival out to termination of the experiment at 65 days. On the other hand, DBA/2 recipients of B10.D2 CD4+ T cells and treated on days 0 and 3 with 0.5 mg D amino acid CDR3-like peptide #1 i.v. exhibited a significantly higher incidence of survival (57%) and a significantly prolonged median survival time of greater than 65 days (p=0.04), compared to the untreated group. This data indicates that D amino acid CDR3-like peptide #1 can have a diminishing effect upon the development of GVHD and alloreactivity of transplanted donor CD4+ T cells.

We claim:

1. A compound consisting of 20 amino acids or less including Ser-Gln-Lys, Ala-Ser-Gln, Asp-Gln-Lys, Gln-Lys-Glu, Lys-Glu-Glu, SEQ ID NO:30, Asn-Gln-Lys, Pro-Arg-Gly, Lys-Gln Ser, Gln-Ser-Ala, Lys-Gln-Asp, Glu-Lys-Gln, Glu-Glu-Lys, SEQ ID NO:66, Lys-Gln-Asn, and Gly-Arg-Pro; wherein said compound inhibits T cell proliferation.

2. A compound according to claim 1 comprising at least an amino acid sequence selected from the group consisting of: SEQ ID NO:15, SEQ ID NO:20, SEQ ID NO:58, SEQ ID NO:41 SEQ ID NO:42, and the reverse amino acid sequence.

3. A compound according to claim 1 that includes at least an amino acid sequence selected from the group consisting of: SEQ ID NO:16, SEQ ID NO:17, SEQ ID NO:18, SEQ ID NO:19, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:59, SEQ ID NO:60, SEQ ID NO:61, SEQ ID NO:62, SEQ ID NO:63, SEQ ID NO:64, SEQ ID NO:65, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 and SEQ ID NO:56, and the reversed amino acid sequences.

4. A compound according to claim 1 wherein amino acids are D amino acids.

5. A compound according to claim 1 comprising less than 10 amino acids.

6. A compound according to claim 1 wherein said compound is circular.

7. A compound according to claim 1 that includes at least two amino acid sequences selected from the group consisting of: Ser-Gln-Lys, Ala-Ser-Gln, Asp-Gln-Lys, Gln-Lys-Glu, Lys-Glu-Glu, SEQ ID NO:30, Asn-Gln-Lys, Pro-Arg-Gly, Lys-Gln Ser, Gln-Ser-Ala, Lys-Gln-Asp, Glu-Lys-Gln, Glu-Glu-Lys, SEQ ID NO:66, Lys-Gln-Asn, and Gly-Arg-Pro.

8. A compound according to claim 1 that includes amino acid sequence Pro-Gly-Pro.

9. A compound according to claim 1 that includes amino acid sequence CPGPEEKRNELEC wherein said amino acids are D amino acids.

10. A compound according to claim 1 that includes an amino acid sequence selected from the group consisting of: SEQ ID NO:57, the reversed amino acid sequence of SEQ ID NO:57, SEQ ID NO:2, the reversed amino acid sequence of SEQ ID NO:2, SEQ ID NO:3, the reversed amino acid sequence of SEQ ID NO:3, SEQ ID NO:4, the reversed amino acid sequence of SEQ ID NO:4, SEQ ID NO:5, the reversed amino acid sequence of SEQ ID NO:5, SEQ ID NO:6, and the reversed amino acid sequence of SEQ ID NO:6.

11. A pharmaceutical composition comprising:
   a) a compound according to claim 1; and
   b) a pharmaceutically acceptable carrier or diluent.

12. A pharmaceutical composition according to claim 11 wherein said compound comprises at least an amino acid sequence selected from the group consisting of: SEQ ID NO:20, and the reverse amino acid sequence.

13. A pharmaceutical composition according to claim 11 wherein said compound includes at least an amino acid sequence selected from the group consisting of: SEQ ID NO:16, SEQ ID NO:17, SEQ ID NO:18, SEQ ID NO:19, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:59, SEQ ID NO:60, SEQ ID NO:61, SEQ ID NO:62, SEQ ID NO:63, SEQ ID NO:64, SEQ ID NO:65, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 and SEQ ID NO:56, and the reversed amino acid sequences.

14. A pharmaceutical composition according to claim 11 wherein said compound comprises D amino acids.

15. A pharmaceutical composition according to claim 11 wherein said compound consists of less than 10 amino acids.

16. A pharmaceutical composition according to claim 11 wherein said compound is circular.

17. A pharmaceutical composition according to claim 11 wherein said compound includes at least two amino acid sequences selected from the group consisting of: Ser-Gln-Lys, Ala-Ser-Gln, Asp-Gln-Lys, Gln-Lys-Glu, Lys-Glu-Glu, SEQ ID NO:30, Asn-Gln-Lys, Pro-Arg-Gly, Lys-Gln Ser, Gln-Ser-Ala, Lys-Gln-Asp, Glu-Lys-Gln, Glu-Glu-Lys, SEQ ID NO:66, Lys-Gln-Asn, and Gly-Arg-Pro.

18. A pharmaceutical composition according to claim 11 wherein said compound further includes amino acid sequence Pro-Gly-Pro.

19. A pharmaceutical composition according to claim 11 wherein said compound includes amino acid sequence CPGPEEKRNELEC and wherein said amino acids are D amino acids.

20. A pharmaceutical composition according to claim 11 wherein said compound includes an amino acid sequence selected from the group consisting of: SEQ ID NQ:57, the reversed amino acid sequence of SEQ ID NO:57, SEQ ID NO:2, the reversed amino acid sequence of SEQ ID NO:2, SEQ ID NO:3, the reversed amino acid sequence of SEQ ID NO:3, SEQ ID NO:4, the reversed amino acid sequence of SEQ ID NO:4, SEQ ID NO:5, the reversed amino acid sequence of SEQ ID NO:5, SEQ ID NO:6, and the reversed amino acid sequence of SEQ ID NO:6.

21. A method of treating an individual suffering from or being susceptible to multiple sclerosis, graft rejection or graft versus host disease comprising the step of administering to said individual a pharmaceutical composition comprising:

a) a therapeutically effective amount of a compound according to claim 1; and b) a pharmaceutically acceptable carrier or diluent.

22. A method according to claim 21 wherein said compound comprises at least an amino acid sequence selected from the group consisting of: SEQ ID NO:15, SEQ ID NO:20, SEQ ID NO:58, SEQ ID NO:41 SEQ ID NO:42, and the reverse amino acid sequences.

23. A method according to claim 21 wherein said compound includes at least an amino acid sequence selected from the group consisting of: SEQ ID NO:16, SEQ ID NO:17, SEQ ID NO:18, SEQ ID NO:19, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:59, SEQ ID NO:60, SEQ ID NO:61, SEQ ID NO:62, SEQ ID NO:63, SEQ ID NO:64, SEQ ID NO:65, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 and SEQ ID NO:56, and the reversed amino acid sequences.

24. A method according to claim 21 wherein said compound comprises D amino acids.

25. A method according to claim 21 wherein said compound consists of less than 10 amino acids.

26. A method according to claim 21 wherein said compound is circular.

27. A method according to claim 21 wherein said compound includes at least two amino acid sequences selected from the group consisting of: Ser-Gln-Lys, Ala-Ser-Gln, Asp-Gln-Lys, Gln-Lys-Glu, Lys-Glu-Glu, SEQ ID NO:30, Asn-Gln-Lys, Pro-Arg-Gly, Lys-Gln Ser, Gln-Ser-Ala, Lys-Gln-Asp, Glu-Lys-Gln, Glu-Glu-Lys, SEQ ID NO:66, Lys-Gln-Asn, and Gly-Arg-Pro.

28. A method according to claim 21 wherein said compound includes amino acid sequence Pro-Gly-Pro.

29. A method according to claim 21 wherein said compound includes amino acid sequence CPGPEEKRNELEC and wherein said amino acids are D amino acids.

30. A method according to claim 21 wherein said compound includes an amino acid sequence selected from the group consisting of: SEQ ID NO:57, the reversed amino acid sequence of SEQ ID NO:57, SEQ ID NO:2, the reversed amino acid sequence of SEQ ID NO:2, SEQ ID NO:3, the reversed amino acid sequence of SEQ ID NO:3, SEQ ID NO:4, the reversed amino acid sequence of SEQ ID NO:4, SEQ ID NO:5, the reversed amino acid sequence of SEQ ID NO:5, SEQ ID NO:6, and the reversed amino acid sequence of SEQ ID NO:6.

31. A method according to claim 21 wherein said condition is selected from the group consisting of systemic lupus erythematosus, rheumatoid arthritis and multiple sclerosis.

* * * * *

UNITED STATES PATENT AND TRADEMARK OFFICE
CERTIFICATE OF CORRECTION

PATENT NO. : 5,958,882
DATED : September 28, 1999
INVENTOR(S) : Bradford A. Jameson et al It is certified that error appears in the above-identified patent and that said Letters Patent is hereby corrected as shown below:

Col. 23, line 40, "espectively" should be
--respectively--

Col. 23, line 41, "ifferences" should be
--differences--

Signed and Sealed this

Twenty-seventh Day of March, 2001

Attest:

NICHOLAS P. GODICI

Attesting Officer

*Acting Director of the United States Patent and Trademark Office*

```
SEQUENCE LISTING (1) GENERAL INFORMATION:

(iii) NUMBER OF SEQUENCES: 66

(2) INFORMATION FOR SEQ ID NO: 1:

(i) SEQUENCE CHARACTERISTICS:
       (A) LENGTH: 13
       (B) TYPE: Amino Acid
       (D) TOPOLOGY: linear (xi) SEQUENCE DESCRIPTION:   SEQ ID NO: 1:

Cys Glu Leu Glu Asn Arg Lys Glu Glu Pro Gly Pro Cys
                 5                  10

(2) INFORMATION FOR SEQ ID NO: 2:

(i) SEQUENCE CHARACTERISTICS:
       (A) LENGTH: 18
       (B) TYPE: Amino Acid
       (D) TOPOLOGY: linear (xi) SEQUENCE DESCRIPTION:   SEQ ID NO: 2:

Cys Glu Val Glu Asp Gln Lys Glu Glu Val Gln Leu Leu Val Phe Gly
                 5                  10                  15

Leu Cys (2) INFORMATION FOR SEQ ID NO: 3:

(i) SEQUENCE CHARACTERISTICS:
       (A) LENGTH: 13
       (B) TYPE: Amino Acid
       (D) TOPOLOGY: linear (xi) SEQUENCE DESCRIPTION:   SEQ ID NO: 3:

Cys Glu Val Glu Asp Gln Lys Glu Glu Pro Gly Pro Cys
                 5                  10

(2) INFORMATION FOR SEQ ID NO: 4:

(i) SEQUENCE CHARACTERISTICS:
       (A) LENGTH: 14
       (B) TYPE: Amino Acid
       (D) TOPOLOGY: linear (xi) SEQUENCE DESCRIPTION:   SEQ ID NO: 4:

Thr Cys Thr Asn Leu Gln Asn Gln Lys Lys Val Glu Cys Lys
                 5                  10

(2) INFORMATION FOR SEQ ID NO: 5:

(i) SEQUENCE CHARACTERISTICS:
```

(A) LENGTH: 11
            (B) TYPE: Amino Acid
            (D) TOPOLOGY: linear (xi) SEQUENCE DESCRIPTION: SEQ ID NO: 5:

Leu Glu Ser Pro Pro Gly Ser Ser Pro Ser Val
                 5                  10

(2) INFORMATION FOR SEQ ID NO: 6:

(i) SEQUENCE CHARACTERISTICS:
            (A) LENGTH: 9
            (B) TYPE: Amino Acid
            (D) TOPOLOGY: linear (ix) FEATURE:
            (D) OTHER INFORMATION: This is a D-amino acid.

(xi) SEQUENCE DESCRIPTION: SEQ ID NO: 6:

Cys Arg Ser Pro Arg Gly Lys Asn Cys
                 5

(2) INFORMATION FOR SEQ ID NO: 7:

(i) SEQUENCE CHARACTERISTICS:
            (A) LENGTH: 18
            (B) TYPE: Amino Acid
            (D) TOPOLOGY: linear (xi) SEQUENCE DESCRIPTION: SEQ ID NO: 7:

Cys Glu Leu Glu Asn Arg Lys Glu Glu Val Glu Trp Val Phe Lys Val
                 5                  10                  15
Thr Cys (2) INFORMATION FOR SEQ ID NO: 8:

(i) SEQUENCE CHARACTERISTICS:
            (A) LENGTH: 18
            (B) TYPE: Amino Acid
            (D) TOPOLOGY: linear (xi) SEQUENCE DESCRIPTION: SEQ ID NO: 8:

Cys Glu Leu Glu Asn Arg Lys Glu Glu Val Glu Trp Val Phe Lys Val
                 5                  10                  15
Thr Phe (2) INFORMATION FOR SEQ ID NO: 9:

(i) SEQUENCE CHARACTERISTICS:
            (A) LENGTH: 19
            (B) TYPE: Amino Acid
            (D) TOPOLOGY: linear (xi) SEQUENCE DESCRIPTION: SEQ ID NO: 9:

Cys Trp Lys Val Phe Thr Leu Glu Val Val Glu Lys Glu Arg Asn Glu
                 5                  10                  15
Glu Leu Cys (2) INFORMATION FOR SEQ ID NO: 10:

(i) SEQUENCE CHARACTERISTICS:
            (A) LENGTH: 17
            (B) TYPE: Amino Acid
            (D) TOPOLOGY: linear (xi) SEQUENCE DESCRIPTION: SEQ ID NO: 10:

Cys Glu Leu Glu Asn Arg Lys Glu Glu Val Glu Trp Val Phe Lys Val

```
                         5             10             15
Cys (2) INFORMATION FOR SEQ ID NO: 11:

(i) SEQUENCE CHARACTERISTICS:
        (A) LENGTH: 17
        (B) TYPE: Amino Acid
        (D) TOPOLOGY: linear (xi) SEQUENCE DESCRIPTION: SEQ ID NO: 11:

His Tyr Lys Leu Ser Gln Arg Gly Tyr Glu Trp Asp Ala Gly Asp Gly
                 5                  10                 15
Cys (2) INFORMATION FOR SEQ ID NO: 12:

(i) SEQUENCE CHARACTERISTICS:
        (A) LENGTH: 18
        (B) TYPE: Amino Acid
        (D) TOPOLOGY: linear (xi) SEQUENCE DESCRIPTION: SEQ ID NO: 12:

Cys Glu Val Glu Asp Gln Lys Glu Glu Val Gln Leu Leu Val Phe Gly
                 5                  10                 15
Leu Thr (2) INFORMATION FOR SEQ ID NO: 13:

(i) SEQUENCE CHARACTERISTICS:
        (A) LENGTH: 18
        (B) TYPE: Amino Acid
        (D) TOPOLOGY: linear (xi) SEQUENCE DESCRIPTION: SEQ ID NO: 13:

Cys Leu Leu Val Phe Glu Val Glu Asp Gln Lys Glu Glu Val Gln Gly
                 5                  10                 15
Leu Cys (2) INFORMATION FOR SEQ ID NO: 14:

(i) SEQUENCE CHARACTERISTICS:
        (A) LENGTH: 23
        (B) TYPE: Amino Acid
        (D) TOPOLOGY: linear (xi) SEQUENCE DESCRIPTION: SEQ ID NO: 14:

Ala Ser Gln Lys Lys Ser Ile Gln Phe His Trp Leu Asn Ser Asn Gln
                 5                  10                 15
Ile Leu Ile Leu Gly Asn Gln
              20

(2) INFORMATION FOR SEQ ID NO:15:

(i) SEQUENCE CHARACTERISTICS:
        (A) LENGTH: 6
        (B) TYPE: Amino Acid
        (D) TOPOLOGY: linear (xi) SEQUENCE DESCRIPTION: SEQ ID NO:15:

Thr Ala Ser Gln Lys Lys
                 5

(2) INFORMATION FOR SEQ ID NO:16:
```

```
    (i) SEQUENCE CHARACTERISTICS:
         (A) LENGTH: 5
         (B) TYPE: Amino Acid
         (D) TOPOLOGY: linear (xi) SEQUENCE DESCRIPTION:  SEQ ID NO:16:

Thr Ala Ser Gln Lys
              5

(2) INFORMATION FOR SEQ ID NO:17:

(i) SEQUENCE CHARACTERISTICS:
         (A) LENGTH: 4
         (B) TYPE: Amino Acid
         (D) TOPOLOGY: linear (xi) SEQUENCE DESCRIPTION:  SEQ ID NO:17:

Ala Ser Gln Lys (2) INFORMATION FOR SEQ ID NO:18:

(i) SEQUENCE CHARACTERISTICS:
         (A) LENGTH: 5
         (B) TYPE: Amino Acid
         (D) TOPOLOGY: linear (xi) SEQUENCE DESCRIPTION:  SEQ ID NO:18:

Ala Ser Gln Lys Lys
              5

(2) INFORMATION FOR SEQ ID NO:19:

(i) SEQUENCE CHARACTERISTICS:
         (A) LENGTH: 4
         (B) TYPE: Amino Acid
         (D) TOPOLOGY: linear (xi) SEQUENCE DESCRIPTION:  SEQ ID NO:19:

Ser Gln Lys Lys (2) INFORMATION FOR SEQ ID NO:20:

(i) SEQUENCE CHARACTERISTICS:
         (A) LENGTH: 7
         (B) TYPE: Amino Acid
         (D) TOPOLOGY: linear (xi) SEQUENCE DESCRIPTION:  SEQ ID NO:20:

Glu Asp Gln Lys Glu Glu Val
              5

(2) INFORMATION FOR SEQ ID NO:21:

(i) SEQUENCE CHARACTERISTICS:
         (A) LENGTH: 4
         (B) TYPE: Amino Acid
         (D) TOPOLOGY: linear (xi) SEQUENCE DESCRIPTION:  SEQ ID NO:21:

Glu Asp Gln Lys (2) INFORMATION FOR SEQ ID NO:22:

(i) SEQUENCE CHARACTERISTICS:
         (A) LENGTH: 5
         (B) TYPE: Amino Acid
         (D) TOPOLOGY: linear
```

5,958,882

33

34

-continued

```
        (xi) SEQUENCE DESCRIPTION: SEQ ID NO:22:

Glu Asp Gln Lys Glu
                5

(2) INFORMATION FOR SEQ ID NO:23:

(i) SEQUENCE CHARACTERISTICS:
           (A) LENGTH: 6
           (B) TYPE: Amino Acid
           (D) TOPOLOGY: linear (xi) SEQUENCE DESCRIPTION: SEQ ID NO:23:

Glu Asp Gln Lys Glu Glu
                5

(2) INFORMATION FOR SEQ ID NO:24:

(i) SEQUENCE CHARACTERISTICS:
           (A) LENGTH: 4
           (B) TYPE: Amino Acid
           (D) TOPOLOGY: linear (xi) SEQUENCE DESCRIPTION: SEQ ID NO:24:

Asp Gln Lys Glu (2) INFORMATION FOR SEQ ID NO:25:

(i) SEQUENCE CHARACTERISTICS:
           (A) LENGTH: 5
           (B) TYPE: Amino Acid
           (D) TOPOLOGY: linear (xi) SEQUENCE DESCRIPTION: SEQ ID NO:25:

Asp Gln Lys Glu Glu
                5

(2) INFORMATION FOR SEQ ID NO:26:

(i) SEQUENCE CHARACTERISTICS:
           (A) LENGTH: 6
           (B) TYPE: Amino Acid
           (D) TOPOLOGY: linear (xi) SEQUENCE DESCRIPTION: SEQ ID NO:26:

Asp Gln Lys Glu Glu Val
                5

(2) INFORMATION FOR SEQ ID NO:27:

(i) SEQUENCE CHARACTERISTICS:
           (A) LENGTH: 4
           (B) TYPE: Amino Acid
           (D) TOPOLOGY: linear (xi) SEQUENCE DESCRIPTION: SEQ ID NO:27:

Gln Lys Glu Glu (2) INFORMATION FOR SEQ ID NO:28:

(i) SEQUENCE CHARACTERISTICS:
           (A) LENGTH: 5
           (B) TYPE: Amino Acid
           (D) TOPOLOGY: linear (xi) SEQUENCE DESCRIPTION: SEQ ID NO:28:

Gln Lys Glu Glu Val
```

```
                              5
(2) INFORMATION FOR SEQ ID NO:29:

(i) SEQUENCE CHARACTERISTICS:
        (A) LENGTH: 4
        (B) TYPE: Amino Acid
        (D) TOPOLOGY: linear (xi) SEQUENCE DESCRIPTION:  SEQ ID NO:29:

Lys Glu Glu Val (2) INFORMATION FOR SEQ ID NO:30:

(i) SEQUENCE CHARACTERISTICS:
        (A) LENGTH: 5
        (B) TYPE: Amino Acid
        (D) TOPOLOGY: linear (xi) SEQUENCE DESCRIPTION:  SEQ ID NO:30:

Ser Pro Pro Gly Ser
                  5

(2) INFORMATION FOR SEQ ID NO:31:

(i) SEQUENCE CHARACTERISTICS:
        (A) LENGTH: 8
        (B) TYPE: Amino Acid
        (D) TOPOLOGY: linear (xi) SEQUENCE DESCRIPTION:  SEQ ID NO:31:

Thr Leu Glu Ser Pro Pro Gly Ser
                  5

(2) INFORMATION FOR SEQ ID NO:32:

(i) SEQUENCE CHARACTERISTICS:
        (A) LENGTH: 9
        (B) TYPE: Amino Acid
        (D) TOPOLOGY: linear (xi) SEQUENCE DESCRIPTION:  SEQ ID NO:32:

Thr Leu Glu Ser Pro Pro Gly Ser Ser
                  5

(2) INFORMATION FOR SEQ ID NO:33:

(i) SEQUENCE CHARACTERISTICS:
        (A) LENGTH: 7
        (B) TYPE: Amino Acid
        (D) TOPOLOGY: linear (xi) SEQUENCE DESCRIPTION:  SEQ ID NO:33:

Leu Glu Ser Pro Pro Gly Ser
                  5

(2) INFORMATION FOR SEQ ID NO:34:

(i) SEQUENCE CHARACTERISTICS:
        (A) LENGTH: 8
        (B) TYPE: Amino Acid
        (D) TOPOLOGY: linear (xi) SEQUENCE DESCRIPTION:  SEQ ID NO:34:

Leu Glu Ser Pro Pro Gly Ser Ser
                  5
```

(2) INFORMATION FOR SEQ ID NO:35:

(i) SEQUENCE CHARACTERISTICS:
        (A) LENGTH: 9
        (B) TYPE: Amino Acid
        (D) TOPOLOGY: linear (xi) SEQUENCE DESCRIPTION: SEQ ID NO:35:

Leu Glu Ser Pro Pro Gly Ser Ser Pro
                5

(2) INFORMATION FOR SEQ ID NO:36:

(i) SEQUENCE CHARACTERISTICS:
        (A) LENGTH: 6
        (B) TYPE: Amino Acid
        (D) TOPOLOGY: linear (xi) SEQUENCE DESCRIPTION: SEQ ID NO:36:

Glu Ser Pro Pro Gly Ser
                5

(2) INFORMATION FOR SEQ ID NO:37:

(i) SEQUENCE CHARACTERISTICS:
        (A) LENGTH: 7
        (B) TYPE: Amino Acid
        (D) TOPOLOGY: linear (xi) SEQUENCE DESCRIPTION: SEQ ID NO:37:

Glu Ser Pro Pro Gly Ser Ser
                5

(2) INFORMATION FOR SEQ ID NO:38:

(i) SEQUENCE CHARACTERISTICS:
        (A) LENGTH: 8
        (B) TYPE: Amino Acid
        (D) TOPOLOGY: linear (xi) SEQUENCE DESCRIPTION: SEQ ID NO:38:

Glu Ser Pro Pro Gly Ser Ser Pro
                5

(2) INFORMATION FOR SEQ ID NO:39:

(i) SEQUENCE CHARACTERISTICS:
        (A) LENGTH: 6
        (B) TYPE: Amino Acid
        (D) TOPOLOGY: linear (xi) SEQUENCE DESCRIPTION: SEQ ID NO:39:

Ser Pro Pro Gly Ser Ser
                5

(2) INFORMATION FOR SEQ ID NO:40:

(i) SEQUENCE CHARACTERISTICS:
        (A) LENGTH: 7
        (B) TYPE: Amino Acid
        (D) TOPOLOGY: linear (xi) SEQUENCE DESCRIPTION: SEQ ID NO:40:

Ser Pro Pro Gly Ser Ser Pro
                5

(2) INFORMATION FOR SEQ ID NO:41:

(i) SEQUENCE CHARACTERISTICS:
    (A) LENGTH: 4
    (B) TYPE: Amino Acid
    (D) TOPOLOGY: linear (xi) SEQUENCE DESCRIPTION: SEQ ID NO:41:

Gln Asn Gln Lys (2) INFORMATION FOR SEQ ID NO:42:

(i) SEQUENCE CHARACTERISTICS:
        (A) LENGTH: 9
        (B) TYPE: Amino Acid
        (D) TOPOLOGY: linear (xi) SEQUENCE DESCRIPTION: SEQ ID NO:42:

Cys Arg Ser Pro Arg Gly Lys Asn Ile
                5

(2) INFORMATION FOR SEQ ID NO:43:

(i) SEQUENCE CHARACTERISTICS:
        (A) LENGTH: 6
        (B) TYPE: Amino Acid
        (D) TOPOLOGY: linear (xi) SEQUENCE DESCRIPTION: SEQ ID NO:43:

Cys Arg Ser Pro Arg Gly
                5

(2) INFORMATION FOR SEQ ID NO:44:

(i) SEQUENCE CHARACTERISTICS:
        (A) LENGTH: 7
        (B) TYPE: Amino Acid
        (D) TOPOLOGY: linear (xi) SEQUENCE DESCRIPTION: SEQ ID NO:44:

Cys Arg Ser Pro Arg Gly Lys
                5

(2) INFORMATION FOR SEQ ID NO:45:

(i) SEQUENCE CHARACTERISTICS:
        (A) LENGTH: 8
        (B) TYPE: Amino Acid
        (D) TOPOLOGY: linear (xi) SEQUENCE DESCRIPTION: SEQ ID NO:45:

Cys Arg Ser Pro Arg Gly Lys Asn
                5

(2) INFORMATION FOR SEQ ID NO:46:

(i) SEQUENCE CHARACTERISTICS:
        (A) LENGTH: 5
        (B) TYPE: Amino Acid
        (D) TOPOLOGY: linear (xi) SEQUENCE DESCRIPTION: SEQ ID NO:46:

Arg Ser Pro Arg Gly
                5

(2) INFORMATION FOR SEQ ID NO:47:

(i) SEQUENCE CHARACTERISTICS:
        (A) LENGTH: 6
        (B) TYPE: Amino Acid (D) TOPOLOGY: linear (xi) SEQUENCE DESCRIPTION: SEQ ID NO:47:

Arg Ser Pro Arg Gly Lys
                    5

(2) INFORMATION FOR SEQ ID NO:48:

(i) SEQUENCE CHARACTERISTICS:
            (A) LENGTH: 7
            (B) TYPE: Amino Acid
            (D) TOPOLOGY: linear (xi) SEQUENCE DESCRIPTION: SEQ ID NO:48:

Arg Ser Pro Arg Gly Lys Asn
                    5

(2) INFORMATION FOR SEQ ID NO:49:

(i) SEQUENCE CHARACTERISTICS:
            (A) LENGTH: 8
            (B) TYPE: Amino Acid
            (D) TOPOLOGY: linear (xi) SEQUENCE DESCRIPTION: SEQ ID NO:49:

Arg Ser Pro Arg Gly Lys Asn Ile
                    5

(2) INFORMATION FOR SEQ ID NO:50:

(i) SEQUENCE CHARACTERISTICS:
            (A) LENGTH: 4
            (B) TYPE: Amino Acid
            (D) TOPOLOGY: linear (xi) SEQUENCE DESCRIPTION: SEQ ID NO:50:

Ser Pro Arg Gly (2) INFORMATION FOR SEQ ID NO:51:

(i) SEQUENCE CHARACTERISTICS:
            (A) LENGTH: 5
            (B) TYPE: Amino Acid
            (D) TOPOLOGY: linear (xi) SEQUENCE DESCRIPTION: SEQ ID NO:51:

Ser Pro Arg Gly Lys
                5

(2) INFORMATION FOR SEQ ID NO:52:

(i) SEQUENCE CHARACTERISTICS:
            (A) LENGTH: 6
            (B) TYPE: Amino Acid
            (D) TOPOLOGY: linear (xi) SEQUENCE DESCRIPTION: SEQ ID NO:52:

Ser Pro Arg Gly Lys Asn
                5

(2) INFORMATION FOR SEQ ID NO:53:

(i) SEQUENCE CHARACTERISTICS:
            (A) LENGTH: 7
            (B) TYPE: Amino Acid
            (D) TOPOLOGY: linear (xi) SEQUENCE DESCRIPTION: SEQ ID NO:53:

```
Ser Pro Arg Gly Lys Asn Ile
                5

(2) INFORMATION FOR SEQ ID NO:54:

(i) SEQUENCE CHARACTERISTICS:
        (A) LENGTH: 4
        (B) TYPE: Amino Acid
        (D) TOPOLOGY: linear (xi) SEQUENCE DESCRIPTION: SEQ ID NO:54:

Pro Arg Gly Lys (2) INFORMATION FOR SEQ ID NO:55:

(i) SEQUENCE CHARACTERISTICS:
        (A) LENGTH: 5
        (B) TYPE: Amino Acid
        (D) TOPOLOGY: linear (xi) SEQUENCE DESCRIPTION: SEQ ID NO:55:

Pro Arg Gly Lys Asn
                5

(2) INFORMATION FOR SEQ ID NO:56:

(i) SEQUENCE CHARACTERISTICS:
        (A) LENGTH: 6
        (B) TYPE: Amino Acid
        (D) TOPOLOGY: linear (xi) SEQUENCE DESCRIPTION: SEQ ID NO:56:

Pro Arg Gly Lys Asn Ile
                5

(2) INFORMATION FOR SEQ ID NO:57:

(i) SEQUENCE CHARACTERISTICS:
        (A) LENGTH: 10
        (B) TYPE: Amino Acid
        (D) TOPOLOGY: linear (xi) SEQUENCE DESCRIPTION: SEQ ID NO:57:

Cys Gln Ser Ala Pro Ala Asp Gln Lys Cys
                5                   10

(2) INFORMATION FOR SEQ ID NO:58:

(i) SEQUENCE CHARACTERISTICS:
        (A) LENGTH: 12
        (B) TYPE: Amino Acid
        (D) TOPOLOGY: linear (xi) SEQUENCE DESCRIPTION: SEQ ID NO:58:

Thr Leu Glu Ser Pro Pro Gly Ser Ser Pro Ser Val
                5                   10

(2) INFORMATION FOR SEQ ID NO:59:

(i) SEQUENCE CHARACTERISTICS:
        (A) LENGTH: 11
        (B) TYPE: Amino Acid
        (D) TOPOLOGY: linear (xi) SEQUENCE DESCRIPTION: SEQ ID NO:59:

Thr Leu Glu Ser Pro Pro Gly Ser Ser Pro Ser
                5                   10
```

(2) INFORMATION FOR SEQ ID NO:60:

(i) SEQUENCE CHARACTERISTICS:
        (A) LENGTH: 10
        (B) TYPE: Amino Acid
        (D) TOPOLOGY: linear (xi) SEQUENCE DESCRIPTION: SEQ ID NO:60:

Leu Glu Ser Pro Pro Gly Ser Ser Pro Ser
                 5                   10

(2) INFORMATION FOR SEQ ID NO:61:

(i) SEQUENCE CHARACTERISTICS:
        (A) LENGTH: 11
        (B) TYPE: Amino Acid
        (D) TOPOLOGY: linear (xi) SEQUENCE DESCRIPTION: SEQ ID NO:61:

Leu Glu Ser Pro Pro Gly Ser Ser Pro Ser Val
                 5                   10

(2) INFORMATION FOR SEQ ID NO:62:

(i) SEQUENCE CHARACTERISTICS:
        (A) LENGTH: 9
        (B) TYPE: Amino Acid
        (D) TOPOLOGY: linear (xi) SEQUENCE DESCRIPTION: SEQ ID NO:62:

Glu Ser Pro Pro Gly Ser Ser Pro Ser
                 5

(2) INFORMATION FOR SEQ ID NO:63:

(i) SEQUENCE CHARACTERISTICS:
        (A) LENGTH: 10
        (B) TYPE: Amino Acid
        (D) TOPOLOGY: linear (xi) SEQUENCE DESCRIPTION: SEQ ID NO:63:

Glu Ser Pro Pro Gly Ser Ser Pro Ser Val
                 5                   10

(2) INFORMATION FOR SEQ ID NO:64:

(i) SEQUENCE CHARACTERISTICS:
        (A) LENGTH: 8
        (B) TYPE: Amino Acid
        (D) TOPOLOGY: linear (xi) SEQUENCE DESCRIPTION: SEQ ID NO:64:

Ser Pro Pro Gly Ser Ser Pro Ser
                 5

(2) INFORMATION FOR SEQ ID NO:65:

(i) SEQUENCE CHARACTERISTICS:
        (A) LENGTH: 9
        (B) TYPE: Amino Acid
        (D) TOPOLOGY: linear (xi) SEQUENCE DESCRIPTION: SEQ ID NO:65:

Ser Pro Pro Gly Ser Ser Pro Ser Val
                 5

-continued

```
(2) INFORMATION FOR SEQ ID NO:66:

(i) SEQUENCE CHARACTERISTICS:
        (A) LENGTH: 5
        (B) TYPE: Amino Acid
        (D) TOPOLOGY: linear (xi) SEQUENCE DESCRIPTION: SEQ ID NO:66:

Ser Gly Pro Pro Ser
```